(12) United States Patent
Theodoridis et al.

(10) Patent No.: US 7,576,224 B2
(45) Date of Patent: *Aug. 18, 2009

(54) INSECTICIDAL (DIHALOPROPENYL) PHENYLALKYL SUBSTITUTED DIHYDROBENZOFURAN AND DIHYDROBENZOPYRAN DERIVATIVES

(75) Inventors: George Theodoridis, Princeton, NJ (US); Edward J. Barron, Trenton, NJ (US); Dominic P. Suarez, Yardley, PA (US); Y. Larry Zhang, Kendall Park, NJ (US); Ping Ding, Lawrenceville, NJ (US); David M. Roush, Princeton, NJ (US); Stephen F. Donovan, Revere, PA (US); Frank J. Zawacki, Yardley, PA (US); Walter H. Yeager, Yardley, PA (US); John W. Lyga, Basking Ridge, NJ (US); Daniel H. Cohen, Princeton, NJ (US)

(73) Assignee: FMC Corporation, Philadelphia, PA (US)

( * ) Notice: Subject to any disclaimer, the term of this patent is extended or adjusted under 35 U.S.C. 154(b) by 175 days.

This patent is subject to a terminal disclaimer.

(21) Appl. No.: 11/292,023

(22) Filed: Dec. 1, 2005

(65) Prior Publication Data
US 2006/0094776 A1 May 4, 2006

Related U.S. Application Data

(62) Division of application No. 10/832,624, filed on Apr. 27, 2004, now Pat. No. 6,987,194.

(60) Provisional application No. 60/466,674, filed on Apr. 30, 2003.

(51) Int. Cl.
C07D 307/80 (2006.01)
C07D 495/10 (2006.01)

(52) U.S. Cl. .................. 549/31; 549/466; D22/120

(58) Field of Classification Search .............. 549/31, 549/466
See application file for complete search history.

(56) References Cited

U.S. PATENT DOCUMENTS

| | | | |
|---|---|---|---|
| 3,474,170 A | 10/1969 | Scharpf et al. | |
| 3,747,171 A | 7/1973 | Montague | |
| 5,360,919 A | 11/1994 | Standen | |
| 5,872,137 A | 2/1999 | Sakamoto et al. | |
| 5,922,880 A | 7/1999 | Sakamoto et al. | |
| 5,952,386 A | 9/1999 | Matsuo et al. | |
| 6,403,639 B1 | 6/2002 | Ishikawa et al. | |
| 6,407,243 B1 | 6/2002 | Bryant et al. | |
| 6,987,194 B2 | 1/2006 | Theodoridis et al. | |
| 7,208,450 B2 | 4/2007 | Theodoridis et al. | |
| 2006/0247283 A1 | 11/2006 | Theodoridis et al. | |
| 2006/0270726 A1 | 11/2006 | Theodoridis et al. | |

FOREIGN PATENT DOCUMENTS

| | | |
|---|---|---|
| EP | 0 648 729 A1 | 4/1995 |
| WO | WO 94/06782 A1 | 4/1994 |
| WO | WO 95/23507 A | 9/1995 |
| WO | WO 96/11909 A | 4/1996 |
| WO | WO 96/33160 A | 10/1996 |
| WO | WO 01/44154 A | 6/2001 |
| WO | WO 01/55141 A1 | 8/2001 |
| WO | WO 2004/006782 A | 1/2004 |
| WO | WO 2004/056735 A | 7/2004 |

OTHER PUBLICATIONS

King, Med Chem: Principle and Practice (1994), p. 206-208.*
Database WPI, Accession No. 1996-263801, Japanese Patent 08 109156 A Abstract.
Supplementary European Search Report, European Patent Application No. EP 04 75 0775, European Patent Office, Munich, search completed on Nov. 30, 2007.
Supplementary European Search Report, European Patent Application No. EP 04 75 0769, European Patent Office, Munich, search completed on Sep. 17, 2007.
Supplementary European Search Report, European Patent Application No. EP 04 76 0587, European Patent Office, Munich, search completed on Sep. 17, 2007.
Supplementary European Search Report, European Patent Application No. EP 04 76 0588, European Patent Office, The Hague, search completed on Jul. 9, 2008.

* cited by examiner

*Primary Examiner*—Taofiq A Solola

(57) ABSTRACT

Insecticidal (dihalopropenyl) phenylalkyl substituted dihydrobenzofuran and dihydrobenzopyran derivatives of Formula I are disclosed. These compounds provide unexpected insecticidal activity across a spectrum of insect pests combined with desirable physical properties including improved photostability.

I

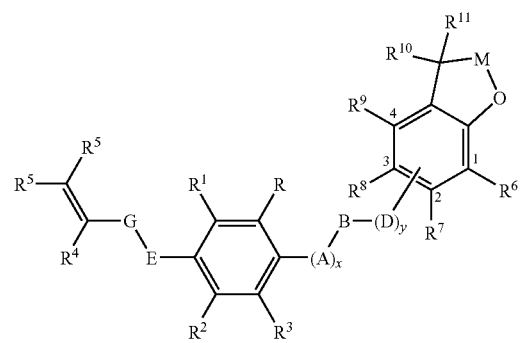

wherein x and y are integers independently selected from 0 or 1; and B is a bridging group

*—(CR$^{16}$R$^{17}$)$_q$—(CR$^{18}$R$^{19}$)$_r$—(CR$^{20}$R$^{21}$)$_s$-
L$_t$-(CR$^{22}$R$^{23}$)$_u$—(CR$^{24}$R$^{25}$)$_v$—(CR$^{26}$R$^{27}$)$_w$—, where the asterisk denotes attachment at A; and q, r, s, u, v and w are integers independently selected from 0, 1 and 2; and t is an integer selected from 0 and 1. A, D, E, G, M, R through R$^{11}$, and R$^{16}$ through R$^{27}$, inclusively, are fully described herein. In addition, compositions comprising an insecticidally effective amount of at least one compound of formula I and methods of controlling insects by applying said compositions to a locus where insects are present or are expected to be present are also disclosed.

3 Claims, No Drawings

INSECTICIDAL (DIHALOPROPENYL) PHENYLALKYL SUBSTITUTED DIHYDROBENZOFURAN AND DIHYDROBENZOPYRAN DERIVATIVES

This application is a divisional of U.S. application Ser. No. 10/832,624, filed Apr. 27, 2004 now U.S. Pat. No. 6,987,194, which claims the benefit of U.S. Provisional Application No. 60/466,674, filed Apr. 30, 2003.

FIELD OF THE INVENTION

The present invention relates to novel compounds and their use in controlling insects and acarids. In particular, it pertains to (dihalopropenyl) phenylalkyl substituted dihydrobenzofuran and dihydrobenzopyran derivatives and agriculturally acceptable salts thereof, compositions containing them and methods for their use in controlling insects and acarids.

BACKGROUND OF THE INVENTION

It is well known that insects can cause significant damage, not only to crops grown in agriculture, such as wheat, corn, soybeans, potatoes, and cotton but also, for example, to structures and turf where the damage is caused by soil-borne insects, such as termites and white grubs. Such damage may result in the loss of millions of dollars of value associated with a given crop, turf or structure. Insecticides and acaricides are useful for controlling such insects and acarids.

A number of patents and publications disclose a variety of dihalopropene compounds that are reported to be insecticidally and acaricidally active. For example, U.S. Pat. No. 5,922,880 discloses certain dihalopropene compounds containing optionally substituted heterocyclic ring groups for use as insecticides and acaricides. Examples of the heterocyclic ring in the optionally substituted heterocyclic ring group are isoxazole, thiazole, 1,3,4-thiadiazole, pyrrole, furan, thiophene, pyrazole, imidazole, 1,2,3-triazole, 1,2,4-triazole, 1,2,3,4-tetrazole, pyridine, pyridazine, pyrimidine, pyrazine, 1,2,4-triazine, 1,3,5-triazine, indole, benzofuran, thianaphthalene, indazole, benzimidazole, benzotriazole, benzisoxazole, benzoxazole, benzothiazole, quinoline, isoquinoline, quinoxaline, quinazole, piperidine, piperazine, tetrahydrofuran, tetrahydropyran, pyrazoline, phthalimide, dioxane, dioxolane, and benzodioxolane (Column 3, lines 15-25).

Insecticides containing dihydrobenzofuranyl substituents are also known in the art. See, in this regard, U.S. Pat. Nos. 3,474,170 and 3,474,171 which disclose dihydrobenzofuranyl esters of carbamic acids.

In addition to activity against target pests a commercially viable pesticide needs to satisfy a number of additional criteria including, inter alia, production costs, environmental impact, mammalian toxicity, lack of undesirable effects on target crops and certain physical characteristics. Desirable physical characteristics for a compound to be used in an outdoor field environment include inter alia, photochemical stability under field conditions. Photostable insecticides and acaricides, i.e., those which do not break down or degrade when exposed to sunlight, are advantageous in that they provide long-term insecticidal and acaricidal activity, which increases the effectiveness of the active compound.

Efficacy problems associated with pesticides that have limited photostability are well known. For example, Clough et al. (Fungicidal β-Methoxyacrylates; Synthesis and Chemistry of Agrochemicals, ACS Symposium Series 504, Chapter 34 (1992)) describes disappointing fungicidal activity of certain compounds when tested in light, and efforts to synthesize fungicides with greater photostability. In another example, Shiokawa, et al. (Chloronicotinyl Insecticides: Development of Imidacloprid; Eighth International Congress of Pesticide Chemistry-Options 2000, ACS Publication 1995) describes the wavelengths of sunlight that reach the earth's surface that can cause photo-degradation of certain compounds such as nitromethylene insecticides and other compounds.

Accordingly, there is a continuing demand for new insecticides and acaricides that are safe, more effective e,g, more photostable, and less costly to prepare on a commercial scale.

SUMMARY OF THE INVENTION

In accordance with the present invention, it has now been found that certain dihalopropenyl phenylalkyl compounds containing a substituted benzo fused heterocycle wherein the heterocycle is either a saturated 5 or 6 membered ring containing one oxygen atom (i.e., a dihydrobenzofuran or a dihydrobenzopyran) are active in the control of insects and acarids. Additionally, these compounds are unexpectedly photochemically stable. The novel compounds are represented by the following general formula I:

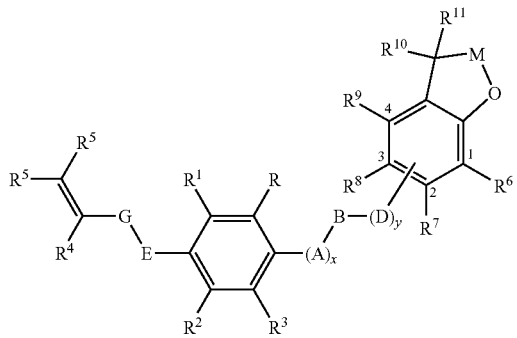

wherein
R and $R^3$ are independently selected from hydrogen, halogen, hydroxy, $(C_1-C_3)$alkyl, $(C_3-C_6)$cycloalkyl, $(C_2-C_5)$alkenyl, $(C_2-C_5)$alkynyl, halo$(C_1-C_3)$alkyl, $(C_1-C_3)$alkoxy, halo$(C_1-C_3)$alkoxy, $(C_1-C_3)$alkylthio, halo$(C_1-C_3)$alkylthio, $(C_1-C_3)$alkylsulfonyl, halo$(C_1-C_3)$alkylsulfonyl, cyano, nitro; optionally substituted amino wherein the optional substituent is selected from $(C_1-C_4)$alkyl, $(C_1-C_3)$alkylcarbonyl and $(C_1-C_3)$alkoxycarbonyl; optionally substituted imidazolyl, optionally substituted imidazolinyl, optionally substituted oxazolinyl, optionally substituted oxazolyl, optionally substituted oxadiazolyl, optionally substituted thiazolyl, optionally substituted pyrazolyl, optionally substituted triazolyl, optionally substituted furanyl, optionally substituted tetrahydrofuranyl, optionally substituted dioxolanyl, optionally substituted dioxanyl, —C(=J)-K, and —C($R^{12}$)-Q-$R^{13}$, wherein the optional substituent is selected from $(C_1-C_4)$alkyl, halo$(C_1-C_4)$alkyl, $(C_1-C_4)$alkoxy, $(C_1-C_4)$alkoxy$(C_1-C_4)$alkyl, $(C_3-C_6)$cycloalkyl, $(C_2-C_5)$alkenyl, $(C_2-C_5)$alkynyl, cyano, nitro and aryl;

where
J is selected from O, S, $NR^{14}$, and $NOR^{14}$, where $R^{14}$ is hydrogen, $(C_1-C_4)$alkyl, halo$(C_1-C_4)$alkyl, aryl and aryl$(C_1-C_4)$alkyl;
K is selected from hydrogen, $(C_1-C_3)$alkyl, halo$(C_1-C_3)$alkyl, $(C_1-C_3)$alkoxy, $(C_1-C_3)$alkylamino and di$(C_1-C_3)$alkylamino;
Q is selected from O, S, and $NR^{14}$, where $R^{14}$ is as previously described;

$R^{12}$ and $R^{13}$ are independently selected from hydrogen, $(C_1-C_4)$alkyl and halo$(C_1-C_4)$alkyl, and $R^{12}$ and $R^{13}$ may be taken together with -T(CHR$^{14}$)$_m$—, where m is an integer of 2 to 4; T is selected from O, S, and NR$^{14}$, where R$^{14}$ is as previously described;

$R^1$ and $R^2$ are independently selected from hydrogen, halogen and $(C_1-C_3)$alkyl;

$R^4$ is hydrogen;

$R^5$'s are independently selected from halogen;

E is selected from CH$_2$, O, S and NR$^{15}$ where R$^{15}$ is selected from hydrogen, $(C_1-C_3)$alkyl, $(C_1-C_3)$alkoxy$(C_1-C_3)$alkyl, aryl$(C_1-C_3)$alkyl, $(C_2-C_4)$alkenyl$(C_1-C_3)$alkyl, halo$(C_2-C_4)$alkenyl$(C_1-C_3)$alkyl, di$(C_1-C_3)$alkylphosphonate, formyl, $(C_1-C_3)$alkylcarbonyl, halo$(C_1-C_3)$alkylcarbonyl, $(C_1-C_3)$alkoxy$(C_1-C_3)$alkylcarbonyl, arylcarbonyl and $(C_1-C_3)$alkylsulfonyl;

G is selected from O, S, CH$_2$O* and (CH$_2$)$_n$ where the asterisk denotes attachment to E, and n is an integer selected from 1 and 2 provided that E and G are not simultaneously O or S, x is an integer selected from 0 or 1;

and when x is 1,

A is selected from O, S(O)$_p$ and —NR$^{15}$, where p is an integer selected from 0, 1 and 2, and R$^{15}$ is as previously described;

B is a bridging group,

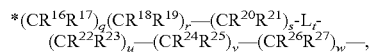

where the asterisk denotes attachment at A; q, r, s, u, v and w are integers independently selected from 0, 1 and 2;

and when q, r, s, u, v or w are 1 or 2, $R^{16}$ through $R^{27}$, inclusively, are independently selected from hydrogen, $(C_1-C_3)$alkyl, halo$(C_1-C_3)$alkyl, $(C_1-C_3)$alkoxy$(C_1-C_3)$alkyl, and $(C_3-C_6)$cycloalkyl;

t is an integer selected from 0 or 1; and when t is 1,

L is selected from CH=CH; O, S(O)$_p$; OS(O)$_2$, S(O)$_2$O, NR$^{28}$; N(oxide)R$^{28}$; NR$^{28}$SO$_2$; NR$^{28}$C(=O)NR$^{29}$; Si(CH$_3$)$_2$; C(=O), OC(=O), NHC(=O); ON=CH; HC=NO; C(=O)O; C(=O)NH; C(=NOR$^{14}$) and [CR$^{30}$R$^{31}$]$_z$, where p is as previously described, R$^{28}$ and R$^{29}$ are independently selected from hydrogen, $(C_1-C_3)$alkyl, $(C_1-C_3)$alkylsulfonyl, $(C_1-C_3)$alkylcarbonyl, $(C_2-C_5)$alkenyl, and $(C_2-C_5)$alkynyl; z is an integer selected from 1 or 2; and R$^{30}$ and R$^{31}$ are independently selected from hydrogen and $(C_1-C_3)$alkyl;

y is an integer selected from 0 or 1;

and when y is 1,

D is selected from O; S(O)$_p$; and NR$^{15}$, where p and R$^{15}$ are as previously described, wherein D is attached to the benzo-fused ring moiety set forth in formula I at any one of the positions designated 1-, 2-, 3- or 4-:

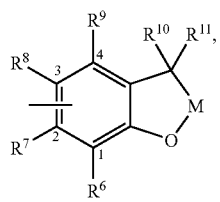

$R^6$, $R^7$, $R^8$ and $R^9$ are independently selected from hydrogen, halogen, $(C_1-C_4)$alkyl, $(C_3-C_6)$cycloalkyl, $(C_2-C_5)$alkenyl, $(C_2-C_5)$alkynyl, halo$(C_1-C_4)$alkyl, $(C_1-C_4)$alkoxy, halo$(C_1-C_4)$alkoxy, $(C_1-C_4)$alkylthio, halo$(C_1-C_4)$alkylthio, $(C_1-C_4)$alkylsulfonyl, halo$(C_1-C_4)$alkylsulfonyl, cyano, nitro, aryl, alkylcarbonylamino, arylcarbonylamino, and $(C_1-C_4)$alkoxycarbonylamino;

$R^{10}$ and $R^{11}$ are independently selected from hydrogen, halogen, hydroxyl, alkyl, haloalkyl, alkoxy, or $R^{10}$ and $R^{11}$ taken together are =O forming a carbonyl group; or —OCH$_2$CH$_2$O— or —SCH$_2$CH$_2$S— forming a ketal or a thioketal group; or NOR$^{15}$ forming an oxime, where R$^{15}$ is as previously described;

M is selected from *C(R$^{32}$R$^{33}$) and *C(R$^{32}$R$^{33}$)C(R$^{34}$R$^{35}$) where the asterisk indicates attachment to O and wherein R$^{32}$ through R$^{35}$ are selected from halogen, $(C_1-C_4)$alkyl, $(C_1-C_4)$alkoxy$(C_1-C_4)$alkyl, and halo$(C_1-C_4)$alkyl;

and agriculturally acceptable salts thereof.

Preferred compounds are the substituted dihydrobenzofuran derivatives—i.e., those where M is *C(R$^{32}$R$^{33}$) and wherein R$^{32}$ and R$^{33}$ are the same and are selected from alkyl, particularly methyl, and halo, particularly fluoro.

The present invention also includes compositions containing an insecticidally effective amount of at least one compound of formula I, and optionally, an effective amount of at least one second compound, with at least one insecticidally compatible carrier.

The present invention also includes methods of controlling insects, in an area where control is desired, which comprise applying an insecticidally effective amount of the above composition to the locus of crops, or other areas where insects are present or are expected to be present.

DETAILED DESCRIPTION OF THE INVENTION

The present invention relates to certain new and useful insecticidal and acaricidal compounds, namely dihalopropenyl phenylalkyl substituted dihydrobenzofurans or dihydrobenzopyrans (hereinafter termed "compounds of formula I") as depicted in general formula I:

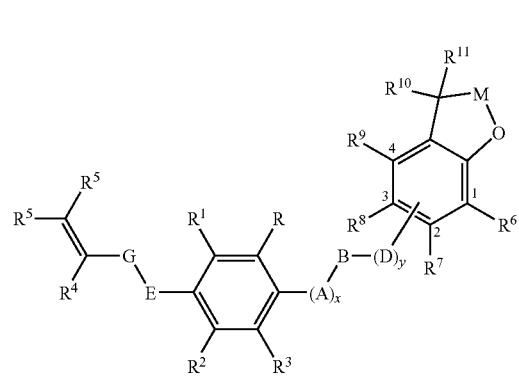

wherein

R and $R^3$ are independently selected from hydrogen, halogen, hydroxy, $(C_1-C_3)$alkyl, $(C_3-C_6)$cycloalkyl, $(C_2-C_5)$alkenyl, $(C_2-C_5)$alkynyl, halo$(C_1-C_3)$alkyl, $(C_1-C_3)$alkoxy, halo$(C_1-C_3)$alkoxy, $(C_1-C_3)$alkylthio, halo$(C_1-$ $C_3$)alkylthio, $(C_1-C_3)$alkylsulfonyl, halo$(C_1-C_3)$alkylsulfonyl, cyano, nitro; optionally substituted amino wherein the optional substituent is selected from $(C_1-C_4)$alkyl, $(C_1-C_3)$alkylcarbonyl and $(C_1-C_3)$alkoxycarbonyl; optionally substituted imidazolyl, optionally substituted imidazolinyl, optionally substituted oxazolinyl, optionally substituted oxazolyl, optionally substituted oxadiazolyl, optionally substituted thiazolyl, optionally substituted pyrazolyl, optionally substituted triazolyl, optionally substituted furanyl, optionally substituted tetrahydrofuranyl, optionally substituted dioxanyl, optionally substituted dioxanyl, —C(=J)-K, and —C($R^{12}$)-Q-$R^{13}$, wherein the optional substituent is selected from $(C_1-C_4)$alkyl, halo$(C_1-C_4)$alkyl, $(C_1-C_4)$alkoxy, $(C_1-C_4)$alkoxy$(C_1-C_4)$alkyl, $(C_3-C_6)$cycloalkyl, $(C_2-C_5)$alkenyl, $(C_2-C_5)$alkynyl, cyano, nitro and aryl;

where
J is selected from O, S, $NR^{14}$, and $NOR^{14}$, where $R^{14}$ is hydrogen, $(C_1-C_4)$alkyl, halo$(C_1-C_4)$alkyl, aryl and aryl$(C_1-C_4)$alkyl;
K is selected from hydrogen, $(C_1-C_3)$alkyl, halo$(C_1-C_3)$alkyl, $(C_1-C_3)$alkoxy, $(C_1-C_3)$alkylamino and di$(C_1-C_3)$alkylamino;
Q is selected from O, S, and $NR^{14}$, where $R^{14}$ is as previously described;
$R^{12}$ and $R^{13}$ are independently selected from hydrogen, $(C_1-C_4)$alkyl and halo$(C_1-C_4)$alkyl, and $R^{12}$ and $R^{13}$ may be taken together with -T(CHR$^{14}$)$_m$—, where m is an integer of 2 to 4; T is selected from O, S, and $NR^{14}$, where $R^{14}$ is as previously described;
$R^1$ and $R^2$ are independently selected from hydrogen, halogen and $(C_1-C_3)$alkyl;
$R^4$ is hydrogen;
$R^5$'s are independently selected from halogen;
E is selected from $CH_2$, O, S and $NR^{15}$ where $R^{15}$ is selected from hydrogen, $(C_1-C_3)$alkyl, $(C_1-C_3)$alkoxy$(C_1-C_3)$alkyl, aryl$(C_1-C_3)$alkyl, $(C_2-C_4)$alkenyl$(C_1-C_3)$alkyl, halo$(C_2-C_4)$alkenyl$(C_1-C_3)$alkyl, di$(C_1-C_3)$alkylphosphonate, formyl, $(C_1-C_3)$alkylcarbonyl, halo$(C_1-C_3)$alkylcarbonyl, $(C_1-C_3)$alkoxy$(C_1-C_3)$alkylcarbonyl, arylcarbonyl and $(C_1-C_3)$alkylsulfonyl;
G is selected from O, S, $CH_2O^*$ and $(CH_2)_n$ where the asterisk denotes attachment to E, and n is an integer selected from 1 and 2 provided that E and G are not simultaneously O or S,
x is an integer selected from 0 or 1;
and when x is 1,
A is selected from O, $S(O)_p$ and —$NR^{15}$, where p is an integer selected from 0, 1 and 2, and $R^{15}$ is as previously described;
B is a bridging group,

*—(CR$^{16}$R$^{17}$)$_q$—(CR$^{18}$R$^{19}$)$_r$—(CR$^{20}$R$^{21}$)$_s$-L$_t$-(CR$^{22}$R$^{23}$)$_u$—(CR$^{24}$R$^{25}$)$_v$—(CR$^{26}$R$^{27}$)$_w$—, where
the asterisk denotes attachment at A; q, r, s, u, v and w are integers independently selected from 0, 1 and 2;

and when q, r, s, u, v or w are 1 or 2,
$R^{16}$ through $R^{27}$, inclusively, are independently selected from hydrogen, $(C_1-C_3)$alkyl, halo$(C_1-C_3)$alkyl, $(C_1-C_3)$alkoxy$(C_1-C_3)$alkyl, and $(C_3-C_6)$cycloalkyl;

t is an integer selected from 0 or 1; and when t is 1,
L is selected from CH=CH; O, $S(O)_p$; $OS(O)_2$, $S(O)_2O$, $NR^{28}$; N(oxide)$R^{28}$; $NR^{28}SO_2$; $NR^{28}C$(=O)$NR^{29}$; Si(CH$_3$)$_2$; C(=O), OC(=O), NHC(=O); ON=CH; HC=NO; C(=O)O; C(=O)NH; C(=NOR$^{14}$) and [CR$^{30}$R$^{31}$]$_z$, where p is as previously described, $R^{28}$ and $R^{29}$ are independently selected from hydrogen, $(C_1-C_3)$alkyl, $(C_1-C_3)$alkylsulfonyl, $(C_1-C_3)$alkylcarbonyl, $(C_2-C_5)$alkenyl, and $(C_2-C_5)$alkynyl; z is an integer selected from 1 or 2; and $R^{30}$ and $R^{31}$ are independently selected from hydrogen and $(C_1-C_3)$alkyl;
y is an integer selected from 0 or 1;
and when y is 1,
D is selected from O; $S(O)_p$; and $NR^{15}$, where p and $R^{15}$ are as previously described, wherein D is attached to the benzo-fused ring moiety set forth in formula I at any one of the positions designated 1-, 2-, 3- or 4-:

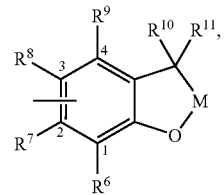

$R^6$, $R^7$, $R^8$ and $R^9$ are independently selected from hydrogen, halogen, $(C_1-C_4)$alkyl, $(C_3-C_6)$cycloalkyl, $(C_2-C_5)$alkenyl, $(C_2-C_5)$alkynyl, halo$(C_1-C_4)$alkyl, $(C_1-C_4)$alkoxy, halo$(C_1-C_4)$alkoxy, $(C_1-C_4)$alkylthio, halo$(C_1-C_4)$alkylthio, $(C_1-C_4)$alkylsulfonyl, halo$(C_1-C_4)$alkylsulfonyl, cyano, nitro, aryl, alkylcarbonylamino, arylcarbonylamino, and $(C_1-C_4)$alkoxycarbonylamino;
$R^{10}$ and $R^{11}$ are independently selected from hydrogen, halogen, hydroxyl, alkyl, alkoxy, or $R^{10}$ and $R^{11}$ taken together are =O forming a carbonyl group; $OCH_2CH_2O$ or $SCH_2CH_2S$ forming a ketal or a thioketal group; or $NOR^{15}$ forming an oxime, where $R^{15}$ is previously described;
M is selected from *C($R^{32}R^{33}$) and *C($R^{32}R^{33}$)C($R^{34}R^{35}$) where the asterisk indicates attachment to O and wherein $R^{32}$ through $R^{35}$ are selected from, halogen, $(C_1-C_4)$alkyl, $(C_1-C_4)$alkoxy$(C_1-C_4)$alkyl, and halo$(C_1-C_4)$alkyl, and agriculturally acceptable salts thereof.
Preferred compounds of formula I are those where
R and $R^3$ are independently selected from halogen and $(C_1-C_3)$alkyl;
$R^1$, $R^2$, and $R^4$ are hydrogen;
$R^5$'s are independently selected from chlorine, bromine, and fluorine;
E is O;
G is $(CH_2)_n$, where n is 1;
x is 1, and A is O;

and
when q, r, s, u, v and w are 1 or 2, $R^{16}$ through $R^{27}$, inclusively, are hydrogen;
t is 0 or 1, and
when t is 1,
L is selected from O, OC(=O), NHC(=O), ON=CH, and CH=NO;
y is 1, and D is selected from O; S(O)$_p$; and NR$^{15}$, where p is 0, and R$^{15}$ is selected from hydrogen, (C$_1$-C$_3$)alkyl, aryl(C$_1$-C$_3$)alkyl, (C$_2$-C$_4$)alkenyl(C$_1$-C$_3$)alkyl, and halo(C$_2$-C$_4$)alkenyl(C$_1$-C$_3$)alkyl, wherein D is attached to the benzo-fused moiety set forth in formula I at the position designated 1 or 4;

R$^6$, R$^7$, R$^8$ and R$^9$ are independently selected from hydrogen, halogen, halo(C$_1$-C$_4$)alkyl and nitro;

R$^{10}$ and R$^{11}$ are hydrogen, or R$^{10}$ and R$^{11}$ taken together are =O forming a carbonyl group;

and

M is C(R$^{32}$R$^{33}$), where R$^{32}$ and R$^{33}$ are independently (C$_1$-C$_4$)alkyl.

Particularly preferred compounds are those of Formula II

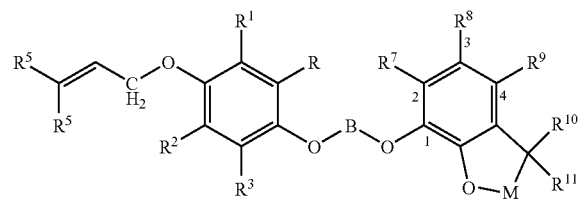

Formula II wherein:

R$^1$ and R$^2$ are hydrogen;

R and R$^3$ are selected from halogen, especially chlorine, and (C$_1$ to C$_3$) alkyl, especially methyl;

R$^5$ is halogen, especially chlorine or bromine;

R$^7$, R$^8$ and R$^9$ are hydrogen, halogen, haloalkyl or nitro, especially hydrogen;

R$^{10}$ and R$^{11}$ are hydrogen or taken together are =O, especially hydrogen;

B is (CH2)n where n is an integer from 2 to 6; and

M is C(R$^{32}$R$^{33}$) where R$^{32}$R$^{33}$ are halogen or (C$_1$-C$_4$)alkyl, especially C$_1$ to C$_4$ alkyl and most especially methyl, Most particularly preferred compounds of formula II are those where R, R$^3$, and R$^5$ are chlorine; n is 3 or 4 and R$^{32}$ and R$^{33}$ are C$_1$ to C$_4$ alkyl. An especially preferred compound is that having the structure of formula III below:

III

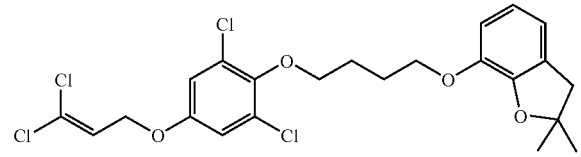

namely 5-(3,3-dichloroprop-2-enyloxy)-2-[4-(2,2-dimethyl (2,3-dihydrobenzo[2,3-b]furan-7-yloxy))butoxy]-1,3-dichlorobenzene.

In addition, in certain cases the compounds of the present invention may possess asymmetric centers, which can give rise to optical enantiomorphs and diastereomers. The compounds may exist in two or more forms, i.e., polymorphs, which are significantly different in physical and chemical properties. The compounds of the present invention may also exist as tautomers, in which migration of a hydrogen atom within the molecule results in two or more structures, which are in equilibrium. The compounds of the present invention may also possess acidic or basic moieties, which may allow for the formation of agriculturally acceptable salts or agriculturally acceptable metal complexes.

This invention includes the use of such enantiomorphs, polymorphs, tautomers, salts and metal complexes. Agriculturally acceptable salts and metal complexes include, without limitation, for example, ammonium salts, the salts of organic and inorganic acids, such as hydrochloric acid, sulfonic acid, ethanesulfonic acid, trifluoroacetic acid, methylbenzenesulfonic acid, phosphoric acid, gluconic acid, pamoic acid, and other acid salts, and the alkali metal and alkaline earth metal complexes with, for example, sodium, potassium, lithium, magnesium, calcium, and other metals.

The methods of the present invention comprise causing an insecticidally effective amount of a compound of formula I to be administered to insects in order to kill or control the insects. Preferred insecticidally effective amounts are those that are sufficient to kill the insect. It is within the scope of the present invention to cause a compound of formula I to be present within insects by contacting the insects with a derivative of that compound, which derivative is converted within the insect to a compound of formula I. This invention includes the use of such compounds, which are referred to as pro-insecticides.

Another aspect of the present invention relates to compositions containing an insecticidally effective amount of at least one compound of formula I.

Another aspect of the present invention relates to compositions containing an insecticidally effective amount of at least one compound of formula I, and an effective amount of at least one second compound.

Another aspect of the present invention relates to methods of controlling insects by applying an insecticidally effective amount of a composition as set forth above to a locus of crops such as, without limitation, cereals, cotton, vegetables, and fruits, or other areas where insects are present or are expected to be present.

The present invention also includes the use of the compounds and compositions set forth herein for control of non-agricultural insect species, for example, dry wood termites and subterranean termites; as well as for use as pharmaceutical agents. In the field of veterinary medicine, the compounds of the present invention are expected to be effective against certain endo- and ecto-parasites, such as insects and worms, which prey on animals. Examples of such animal parasites include, without limitation, *Gastrophilus* spp., *Stomoxys* spp., *Trichodectes* spp., *Rhodnius* spp., *Ctenocephalides canis*, and other species.

As used in this specification and unless otherwise indicated the substituent terms "alkyl" and "alkoxy", used alone or as part of a larger moiety, includes straight or branched chains of at least one or two carbon atoms, as appropriate to the substituent, and preferably up to 12 carbon atoms, more preferably up to ten carbon atoms, most preferably up to seven carbon atoms. The term "alkenyl" and "alkynyl" used alone or as part of a larger moiety, includes straight or branched chains of at least two carbon atoms containing at least one carbon-carbon double bond or triple bond, and preferably up to 12 carbon atoms, more preferably up to ten carbon atoms, most preferably up to seven carbon atoms. The term "aryl" refers to an aromatic ring structure, including fused rings, having six to ten carbon atoms, for example, phenyl or naphthyl. The term "heteroaryl" refers to an aromatic ring structure, including fused rings, in which at least one of the atoms is other than carbon, for example, without limitation, sulfur, oxygen, or nitrogen. The term "GC analysis" refers to gas chromatographic analysis of; while the term "TLC analysis" refers to thin layer chromatographic analysis of, for example a reaction mixture. The term "HPLC" refers to high pressure liquid chromatography, as it relates to, for example a method of separating components from a reaction mixture. The term "DMF" refers to N,N-dimethylformamide. The term "THF" refers to tetrahydrofuran. The term "halogen" or "halo" refers to fluorine, bromine, iodine, or chlorine. The term "ambient temperature" or "room temperature" often abbreviated as "RT", for example, in reference to a chemical reaction mixture temperature, refers to a temperature in the range of 20° C. to 30° C. The term "insecticidal" or "acaricidal", "insecticide" or "acaricide" refers to a compound of the present invention, either alone or in admixture with at least one of a second compound, or with at least one compatible carrier, which causes the destruction or the inhibition of action of insects or acarids. The term "independently selected from" as set forth above and in the claims section of the present specification refers to the possibility that moieties, for example the $R^5$'s, may be the same or they may be different within the group that the selection is made.

The substituted arylalkene derivatives of formula I can be synthesized by methods that are individually known to one skilled in the art from available intermediate compounds.

Scheme 1 below illustrates a general procedure for synthesizing substituted arylalkene compounds of formula I, inter alia, where, for example, $R^1$, $R^2$, $R^4$, $R^7$, $R^8$, $R^9$, $R^{10}$ and $R^{11}$ are hydrogen; R, $R^3$ and $R^5$'s are chloro; M is —C($R^{32}R^{33}$)—, where $R^{32}$ and $R^{33}$ are methyl; q, r, s and u are 1, where $R^{16}$, $R^{17}$, $R^{18}$, $R^{19}$ $R^{20}$, $R^{21}$, $R^{22}$ and $R^{23}$ are hydrogen, t, v and w are 0; x and y are 1; A, D and E are O, where D is attached to the benzo-fused ring at the position designated as 1; and G is $(CH_2)_n$ where n is 1;

Scheme 1

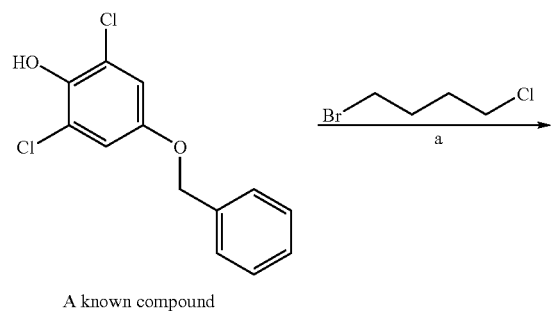

A known compound

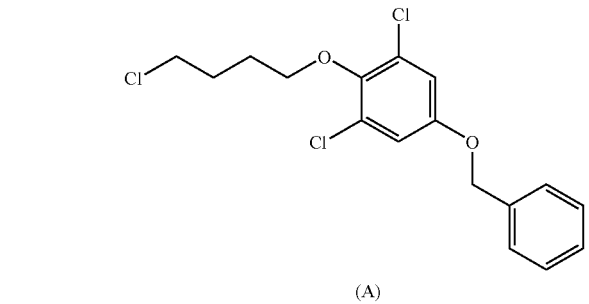

(A)

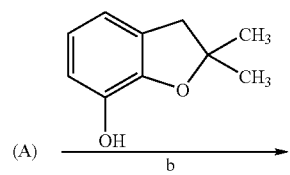

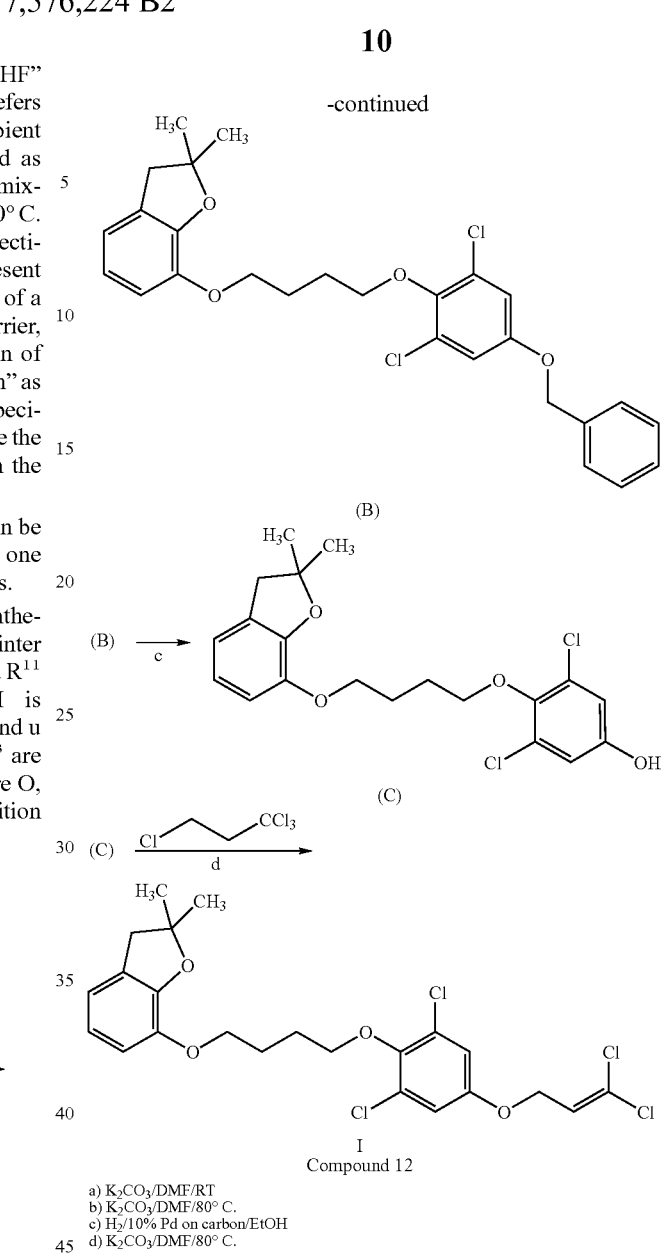

a) $K_2CO_3$/DMF/RT
b) $K_2CO_3$/DMF/80° C.
c) $H_2$/10% Pd on carbon/EtOH
d) $K_2CO_3$/DMF/80° C.

In a first step as depicted in Scheme 1, an appropriately substituted phenol, for example, the known compound 2,6-dichloro-4-phenylmethoxyphenol, was reacted under basic conditions with a haloalkane derivative of a desired carbon chain length, for example 1-bromo-4-chlorobutane, to attach the bridging group B, thereby affording the corresponding 1,3-dichloro-2-(4-chlorobutoxy)-5-(phenylmethoxy)benzene (A). Intermediate (A) was then reacted under basic conditions with, for example, the known compound 2,2-dimethyl-2,3-dihydrobenzo[b]furan-7-ol, to attach moiety D, as well as the benzo-fused ring, affording the corresponding 2-[4-(2,2-dimethyl-(2,3-dihydrobenzo[2,3-b]furan-7-yloxy))butoxy]-1,3-dichloro-5-(phenylmethoxy)benzene (B). Intermediate (B), for example 2-[4-(2,2-dimethyl-(2,3-dihydrobenzo[2,3-b]furan-7-yloxy))butoxy]-1,3-dichloro-5-(phenylmethoxy)benzene, as set forth above, was then reduced with hydrogen gas in the presence of a catalyst, for example 10% palladium on carbon, providing the corresponding 4-[4-(2,2-dimethyl(2,3-dihydrobenzo[2,3-b]furan-7-yloxy))butoxy]-3,5-dichlorophenol (C). Intermediate (C) was then reacted under basic conditions with, for example, 1,1,1,3-tetrachloropropane, which simultaneously dehydrohalogenates, thereby introducing the moiety -E-G-C($R^4$)=C($R^5$)($R^5$) into the molecule to provide Compound 12, a novel compound of formula I. Example 1 set forth below, provides a detailed method to how Compound 12 shown in Scheme 1 was prepared.

Scheme 2 below illustrates a general procedure for synthesizing substituted arylalkene derivatives of formula I, inter alia, where, for example, $R^1$, $R^2$, $R^4$, $R^7$, $R^8$ and $R^9$ are hydrogen; $R^{10}$ and $R^{11}$ are taken together with O to form a carbonyl group; R, $R^3$ and $R^5$'s are chloro; M is —C($R^{32}R^{33}$)—, where $R^{32}$ and $R^{33}$ are methyl; q, r, s and u are 1, where $R^{16}$, $R^{17}$, $R^{18}$, $R^{19}R^{20}$, $R^{21}$, $R^{22}$ and $R^{23}$ are hydrogen, t, v and w are 0; x and y are 1; A, D and E are O, where D is attached to the benzo-fused ring at the position designated as 1; and G is $(CH_2)_n$ where n is 1;

Scheme 2

Compound 12

Compound 36 e) $K_2S_2O_8$/$CuSO_4$/$CH_3CN$/$H_2O$

As depicted in Scheme 2, certain compounds of the present invention, i.e., compounds of formula I, may be further reacted to provide additional compounds of formula I. For example, Compound 12 was oxidized with potassium persulfate and copper sulfate pentahydrate, affording the corresponding ketone derivative (Compound 36), where $R^{10}$ and $R^{11}$ are taken together with O to form a carbonyl group. Example 2 set forth below, provides a detailed method to how Compound 36 shown in Scheme 2 was prepared.

Scheme 3 below illustrates a general procedure for synthesizing substituted arylalkene compounds of formula I, where, for example, $R^1$, $R^2$, $R^4$, $R^{10}$ and $R^{11}$ are hydrogen; $R^7$, $R^8$ or $R^9$ may be a substituent other that hydrogen, for example $R^8$ is trifluoromethyl; R, $R^3$ and $R^5$'s are chloro; M is —C($R^{32}R^{33}$)—, where $R^{32}$ and $R^{33}$ are methyl; q, r, s and u are 1, where $R^{16}$, $R^{17}$, $R^{18}$, $R^{19}R^{20}$, $R^{21}$, $R^{22}$ and $R^{23}$ are hydrogen, t, v and w are 0; x and y are 1; A, D and E are O, where D is attached to the benzo-fused ring at the position designated as 1; and G is $(CH_2)_n$ where n is 1;

Scheme 3

Known compound (D)

(D) →g (E)

(E) →h (F)

(F) →i (G)

Known compound

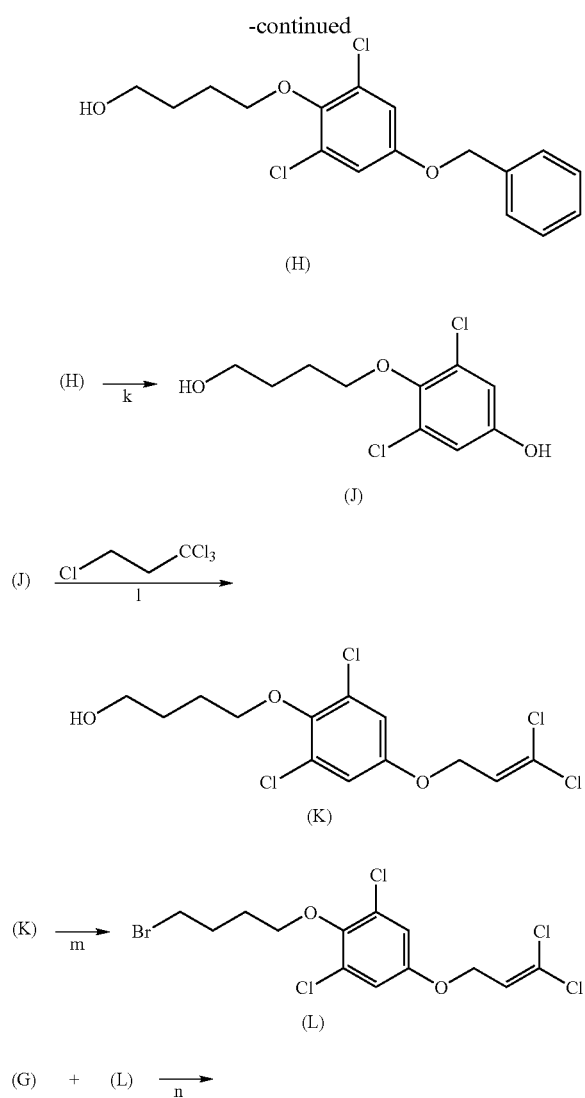

drobenzo[2,3-b]furan-7-yl acetate was reduced by hydrogenation under catalytic conditions affording the corresponding 5-amino intermediate (D). Intermediate (D) was then treated with tert-butyl nitrite, then halogenated with, for example elemental iodine, yielding the corresponding 5iodo-2,2-dimethyl-2,3-dihydrobenzo[2,3-b]furan-7-yl acetate (E). Intermediate (E) was in turn haloalkylated with 2,2-difluoro-2-fluorosulfonyl acetate and copper iodide, providing the corresponding 2,2-dimethyl-5-(trifluoromethyl)-2,3-dihydrobenzo[2,3-b]furan-7-yl acetate (F), which was in turn deprotected by treating it with strong base, affording the corresponding 2,2-dimethyl-5-(trifluoromethyl)-2,3-dihydrobenzo[2,3-b]furan-7-ol (G).

In a second series of steps, 2,6-dichloro-4-phenylmethoxyphenol (known compound) was reacted under basic conditions with, for example 4-chlorobutan-1-ol, as a means of attaching bridging group B, yielding the corresponding intermediate 4-[2,6-dichloro-4-(phenylmethoxy)phenoxy]butan-1-ol (H). Intermediate (H) was then de-protected by cleavage of the phenylmethyl moiety using hydrogenation under catalytic conditions affording the corresponding phenol intermediate (J), which was in turn reacted with, for example 1,1,1,3-tetrachloropropane under basic conditions, affording the corresponding butanol intermediate (K). Intermediate (K) was then brominated with, for example carbon tetrabromide and triphenylphosphine, providing the corresponding bromobutane intermediate (L). Intermediate (L) was in turn reacted with intermediate (G) under basic conditions, affording a compound of formula I where, for example $R^8$ is trifluoromethyl (Compound 20). Example 3 set forth below, provides a detailed method to how Compound 20 shown in Scheme 3 was prepared.

Scheme 4 below illustrates a general procedure for synthesizing substituted arylalkene compounds of formula I where, for example, $R^1$, $R^2$, $R^4$, $R^7$, $R^8$, $R^9$, $R^{10}$ and $R^{11}$ are hydrogen; R, $R^3$ and $R^5$'s are chloro; M is —$C(R^{32}R^{33})$—, where $R^{32}$ and $R^{33}$ are methyl; q, r s and t are 1, where $R^{16}$, $R^{17}$, $R^{18}$, $R^{19}$ $R^{20}$, and $R^{21}$ are hydrogen and L is NHC(=O), u, v and w are 0; x and y are 1; A, D and E are O, where D is attached to the benzo-fused ring at the position designated as 1; and G is $(CH_2)_n$ where n is 1;

Scheme 4

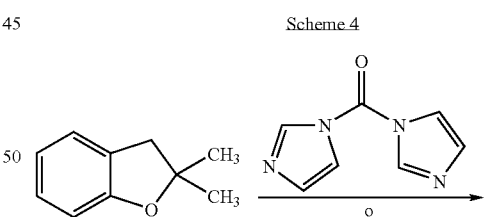

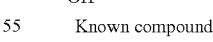

Known compound

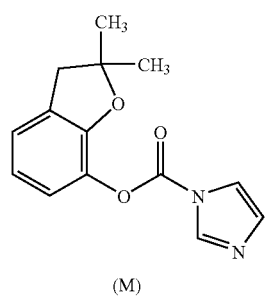

(M)

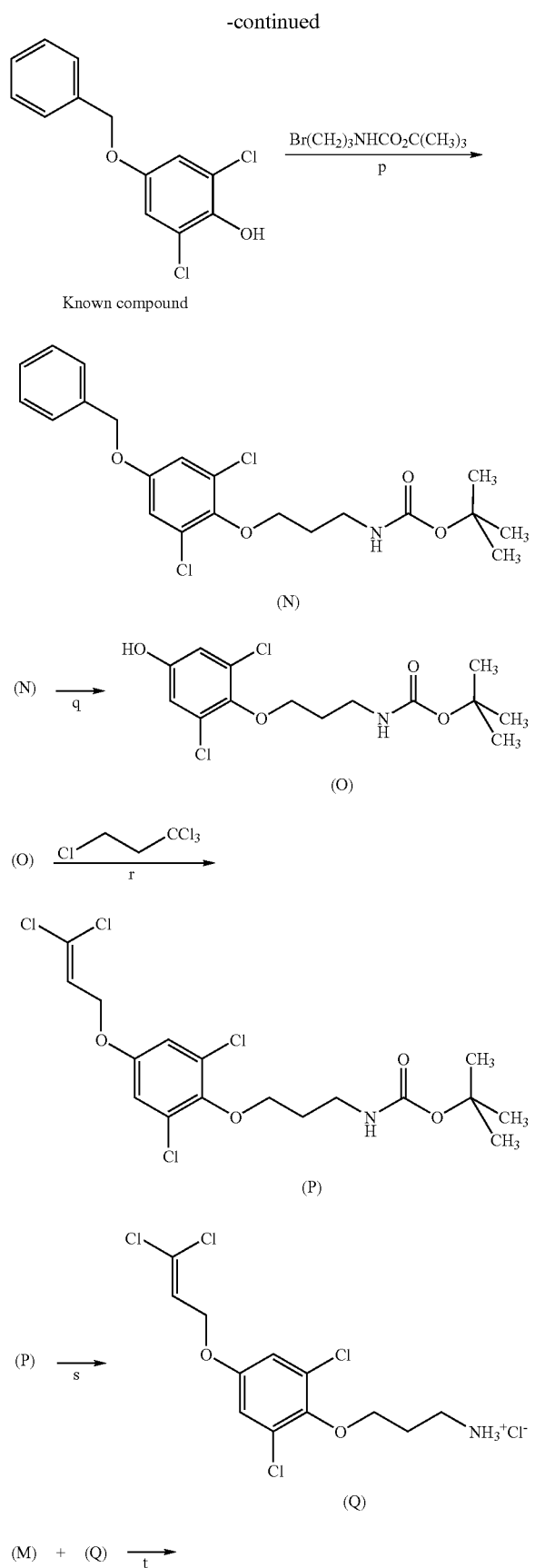
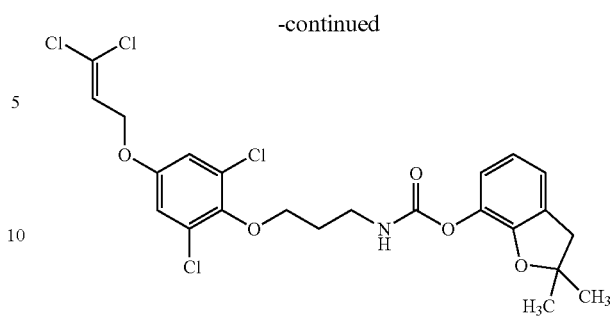

Compound 53 o) CH$_2$Cl$_2$/RT
p) K$_2$CO$_3$/DMF
q) H$_2$/10% Pd on C/1:1 EtOAc—C$_2$H$_5$OH/RT
r) K$_2$CO$_3$/DMF/RT -80° C.
s) 2N HCl in Et$_2$O
t) Et$_3$N/CH$_2$Cl$_2$/CH$_3$CN

Scheme 4, as depicted provides a route to the compounds of the present invention where, inter alia, t is 1 and L is, for example a moiety such as NHC(=O). Accordingly, as a first step 2,2-dimethyl-2,3-dihydrobenzo[2,3-b]furan-7-yl imidazolecarboxylate (M) was prepared by protecting the hydroxy group of 2,2-dimethyl-2,3-dihydrobenzo[2,3-b]furan-7-ol by reacting it with 1,1'-carbonyldiimidazole.

In another series of reactions, 2,6-dichloro-4-phenylmethoxyphenol was first reacted with, for example (tert-butoxy)-N-(3-bromopropyl)carboxamide under basic conditions, providing N-{3-[2,6-dichloro-4-(phenylmethoxy)phenoxy]propyl}(tert-butoxy)carboxamide (N). Intermediate (N) was then de-protected by cleavage of the phenylmethyl moiety using hydrogenation under catalytic conditions affording the corresponding phenol intermediate (O), which was in turn reacted with, for example 1,1,1,3-tetrachloropropane under basic conditions, affording the corresponding carboxamide intermediate (P). Cleavage of the tert-butoxycarbonyl moiety from intermediate (P) under acidic conditions yielded, for example the amine hydrochloride salt intermediate (O), which was then reacted with intermediate (M) under basic conditions, affording a compound of formula I where, for example L is NHC(=O) (Compound 53). Example 4 set forth below, provides a detailed method to how Compound 53 shown in Scheme 4 was prepared.

One skilled in the art will, of course, recognize that the formulation and mode of application of a toxicant may affect the activity of the material in a given application. Thus, for agricultural use the present insecticidal compounds may be formulated as a granular of relatively large particle size (for example, 8/16 or 4/8 US Mesh), as water-soluble or water-dispersible granules, as powdery dusts, as wettable powders, as emulsifiable concentrates, as aqueous emulsions, as solutions, or as any of other known types of agriculturally-useful formulations, depending on the desired mode of application. It is to be understood that the amounts specified in this specification are intended to be approximate only, as if the word "about" were placed in front of the amounts specified.

These insecticidal compositions may be applied either as water-diluted sprays, or dusts, or granules to the areas in which suppression of insects is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the insecticidal compound and 99.0 parts of talc.

Wettable powders, also useful formulations for insecticides, are in the form of finely divided particles that disperse readily in water or other dispersant. The wettable powder is ultimately applied to the locus where insect control is needed either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.0 parts of the insecticidal compound, 17.9 parts of Palmetto clay, and 1.0 part of sodium lignosulfonate and 0.3 part of sulfonated aliphatic polyester as wetting agents. Additional wetting agent and/or oil will frequently be added to a tank mix for to facilitate dispersion on the foliage of the plant.

Other useful formulations for insecticidal applications are emulsifiable concentrates (ECs) which are homogeneous liquid compositions dispersible in water or other dispersant, and may consist entirely of the insecticidal compound and a liquid or solid emulsifying agent, or may also contain a liquid carrier, such as xylene, heavy aromatic naphthas, isphorone, or other non-volatile organic solvents. For insecticidal application these concentrates are dispersed in water or other liquid carrier and normally applied as a spray to the area to be treated. The percentage by weight of the essential active ingredient may vary according to the manner in which the composition is to be applied, but in general comprises 0.5 to 95% of active ingredient by weight of the insecticidal composition.

Flowable formulations are similar to ECs, except that the active ingredient is suspended in a liquid carrier, generally water. Flowables, like ECs, may include a small amount of a surfactant, and will typically contain active ingredients in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

Other useful formulations include suspensions of the active ingredient in a relatively non-volatile solvent such as water, corn oil, kerosene, propylene glycol, or other suitable solvents.

Still other useful formulations for insecticidal applications include simple solutions of the active ingredient in a solvent in which it is completely soluble at the desired concentration, such as acetone, alkylated naphthalenes, xylene, or other organic solvents. Granular formulations, wherein the toxicant is carried on relative coarse particles, are of particular utility for aerial distribution or for penetration of cover crop canopy. Pressurized sprays, typically aerosols wherein the active ingredient is dispersed in finely divided form as a result of vaporization of a low-boiling dispersant solvent carrier may also be used. Water-soluble or water-dispersible granules are free flowing, non-dusty, and readily water-soluble or water-miscible. In use by the farmer on the field, the granular formulations, emulsifiable concentrates, flowable concentrates, aqueous emulsions, solutions, etc., may be diluted with water to give a concentration of active ingredient in the range of say 0.1% or 0.2% to 1.5% or 2%.

The active insecticidal compounds of this invention may be formulated and/or applied with one or more second compounds. Such combinations may provide certain advantages, such as, without limitation, exhibiting synergistic effects for greater control of insect pests, reducing rates of application of insecticide thereby minimizing any impact to the environment and to worker safety, controlling a broader spectrum of insect pests, safening of crop plants to phytotoxicity, and improving tolerance by non-pest species, such as mammals and fish.

Second compounds include, without limitation, other pesticides, plant growth regulators, fertilizers, soil conditioners, or other agricultural chemicals. In applying an active compound of this invention, whether formulated alone or with other agricultural chemicals, an effective amount and concentration of the active compound is of course employed; the amount may vary in the range of, e.g. about 0.001 to about 3 kg/ha, preferably about 0.03 to about 1 kg/ha. For field use, where there are losses of insecticide, higher application rates (e.g., four times the rates mentioned above) may be employed.

When the active insecticidal compounds of the present invention are used in combination with one or more of second compounds, e.g., with other pesticides such as herbicides, the herbicides include, without limitation, for example: N-(phosphonomethyl)glycine ("glyphosate"); aryloxyalkanoic acids such as (2,4-dichlorophenoxy)acetic acid ("2,4-D"), (4-chloro-2-methylphenoxy)acetic acid ("MCPA"), (+/−)-2-(4chloro-2-methylphenoxy)propanoic acid ("MCPP"); ureas such as N,N-dimethyl-N'-[4-(1-methylethyl)phenyl]urea ("isoproturon"); imidazolinones such as 2-[4,5-dihydro-4-methyl-4-(1-methylethyl)-5-oxo-1H-imidazol-2-yl]-3-pyridinecarboxylic acid ("imazapyr"), a reaction product comprising (+/−)-2-[4,5-dihydro-4-methyl-4-(1-methylethyl)-5-oxo-1H-imidazol-2-yl]-4-methylbenzoic acid and (+/−)2-[4,5-dihydro-4-methyl-4-(1-methylethyl)-5-oxo-1H-imidazol-2-yl]-5-methylbenzoic acid ("imazamethabenz"), (+/−)-2-[4,5-dihydro-4-methyl-4-(1-methylethyl)-5-oxo-1H-imidazol-2-yl]-5-ethyl-3-pyridinecarboxylic acid ("imazethapyr"), and (+/−)-2-[4,5-dihydro-4-methyl-4-(1-methylethyl)-5-oxo-1H-imidazol-2-yl]-3-quinolinecarboxylic acid ("imazaquin"); diphenyl ethers such as 5-[2-chloro-4-(trifluoromethyl)phenoxy]-2-nitrobenzoic acid ("acifluorfen"), methyl 5-(2,4-dichlorophenoxy)-2-nitrobenzoate ("bifenox"), and 5-[2-chloro-4-(trifluoromethyl)phenoxy]-N-(methylsulfonyl)-2-nitrobenzamide ("fomasafen"); hydroxybenzonitriles such as 4-hydroxy-3,5-diiodobenzonitrile ("ioxynil") and 3,5-dibromo-4-hydroxybenzonitrile ("bromoxynil"); sulfonylureas such as 2-[[[[(4chloro-6-methoxy-2-pyrimidinyl)amino]carbonyl]amino]sulfonyl]benzoic acid ("chlorimuron"), 2-chloro-N-[[(4-methoxy-6-methyl-1,3,5-triazin-2-yl)amino]carbonyl]benzenesulfonamide ("chlorsulfuron"), 2-[[[[[(4,6-dimethoxy-2-pyrimidinyl)amino]carbonyl]amino]sufonyl]methyl]benzoic acid ("bensulfuron"), 2-[[[[(4,6-dimethoxy-2-pyrimidinyl)amino]carbonyl]amino]sulfonyl]-1-methy-1H-pyrazol-4-carboxylic acid ("pyrazosulfuron"), 3-[[[[(4-methoxy-6-methyl-1,3,5-triazin-2-yl)amino]carbonyl]amino]sulfonyl]-2-thiophenecarboxylic acid ("thifensulfuron"), and 2-(2-chloroethoxy)-N [[(4-methoxy-6-methyl-1,3,5-triazin-2-yl)amino]carbonyl] benzenesulfonamide ("triasulfuron"); 2-(4-aryloxyphenoxy)alkanoic acids such as (+/−)-2[4-[(6-chloro-2- benzoxazolyl)oxy]phenoxy]-propanoic acid (fenoxaprop"), (+/−)-2-[4[[5-(trifluoromethyl)-2-pyridinyl]oxy]-phenoxy] propanoic acid ("fluazifop"), (+/−)-2-[4-(6chloro-2-quinoxalinyl)oxy]-phenoxy]propanoic acid ("quizalofop"), and (+/−)-2-[(2,4-dichlorophenoxy)phenoxy]propanoic acid ("diclofop"); benzothiadiazinones such as 3-(1-methylethyl)-1H-1,2,3-benzothiadiazin-4(3H)-one-2,2-dioxide ("bentazone"); 2-chloroacetanilides such as N-(butoxymethyl)-2-chloro-N-(2,6-diethylphenyl)acetamide ("butachlor"), 2-chloro-N-(2-ethyl-6-methylphenyl)-N-(2-methoxy-1-methylethyl)acetamide ("metolachlor"), 2-chloro-N-(ethoxymethyl)-N-(2-ethyl-6-methylphenyl)acetamide ("acetochlor"), and (RS)-2-chloro-N-(2,4-dimethyl-3-thienyl)-N-(2-methoxy-1-methylethyl)acetamide ("dimethenamide"); arenecarboxylic acids such as 3,6-dichloro-2-methoxybenzoic acid ("dicamba"); pyridyloxyacetic acids such as [(4-amino-3,5-dichloro-6-fluoro-2-pyridinyl)oxy]acetic acid ("fluroxypyr"), and other herbicides.

When the active insecticidal compounds of the present invention are used in combination with one or more of second compounds, e.g., with other pesticides such as other insecticides, the other insecticides include, for example: organophosphate insecticides, such as chlorpyrifos, diazinon, dimethoate, malathion, parathion-methyl, and terbufos; pyrethroid insecticides, such as fenvalerate, deltamethrin, fenpropathrin, cyfluthrin, flucythrinate, alpha-cypermethrin, bifenthrin, cypermethrin, resolved cyhalothrin, etofenprox, esfenvalerate, tralomehtrin, tefluthrin, cycloprothrin, betacyfluthrin, and acrinathrin; carbamate insecticides, such as aldecarb, carbaryl, carbofuran, and methomyl; organochlorine insecticides, such as endosulfan, endrin, heptachlor, and lindane; benzoylurea insecticides, such as diflubenuron, triflumuron, teflubenzuron, chlorfluazuron, flucycloxuron, hexaflumuron, flufenoxuron, and lufenuron; and other insecticides, such as amitraz, clofentezine, fenpyroximate, hexythiazox, spinosad, and imidacloprid.

When the active insecticidal compounds of the present invention are used in combination with one or more of second compounds, e.g., with other pesticides such as fungicides, the fungicides include, for example: benzimidazole fungicides, such as benomyl, carbendazim, thiabendazole, and thiophanate-methyl; 1,2,4-triazole fungicides, such as epoxyconazole, cyproconazole, flusilazole, flutriafol, propiconazole, tebuconazole, triadimefon, and triadimenol; substituted anilide fungicides, such as metalaxyl, oxadixyl, procymidone, and vinclozolin; organophosphorus fungicides, such as fosetyl, iprobenfos, pyrazophos, edifenphos, and tolclofos-methyl; morpholine fungicides, such as fenpropimorph, tridemorph, and dodemorph; other systemic fungicides, such as fenarimol, imazalil, prochloraz, tricyclazole, and triforine; dithiocarbamate fungicides, such as mancozeb, maneb, propineb, zineb, and ziram; non-systemic fungicides, such as chlorothalonil, dichlofluanid, dithianon, and iprodione, captan, dinocap, dodine, fluazinam, gluazatine, PCNB, pencycuron, quintozene, tricylamide, and validamycin; inorganic fungicides, such as copper and sulphur products, and other fungicides.

When the active insecticidal compounds of the present invention are used in combination with one or more of second compounds, e.g., with other pesticides such as nematicides, the nematicides include, for example: carbofuran, carbosulfan, turbufos, aldicarb, ethoprop, fenamphos, oxamyl, isazofos, cadusafos, and other nematicides.

When the active insecticidal compounds of the present invention are used in combination with one or more of second compounds, e.g., with other materials such as plant growth regulators, the plant growth regulators include, for example: maleic hydrazide, chlormequat, ethephon, gibberellin, mepiquat, thidiazon, inabenfide, triaphenthenol, paclobutrazol, unaconazol, DCPA, prohexadione, trinexapac-ethyl, and other plant growth regulators.

Soil conditioners are materials which, when added to the soil, promote a variety of benefits for the efficacious growth of plants. Soil conditioners are used to reduce soil compaction, promote and increase effectiveness of drainage, improve soil permeability, promote optimum plant nutrient content in the soil, and promote better pesticide and fertilizer incorporation. When the active insecticidal compounds of the present invention are used in combination with one or more of second compounds, e.g., with other materials such as soil conditioners, the soil conditioners include organic matter, such as humus, which promotes retention of cation plant nutrients in the soil; mixtures of cation nutrients, such as calcium, magnesium, potash, sodium, and hydrogen complexes; or microorganism compositions which promote conditions in the soil favorable to plant growth. Such microorganism compositions include, for example, *bacillus, pseudomonas, azotobacter, azospirillum, rhizobium*, and soil-borne *cyanobacteria*.

Fertilizers are plant food supplements, which commonly contain nitrogen, phosphorus, and potassium. When the active insecticidal compounds of the present invention are used in combination with one or more of second compounds, e.g., with other materials such as fertilizers, the fertilizers include nitrogen fertilizers, such as ammonium sulfate, ammonium nitrate, and bone meal; phosphate fertilizers, such as superphosphate, triple superphosphate, ammonium sulfate, and diammonium sulfate; and potassium fertilizers, such as muriate of potash, potassium sulfate, and potassium nitrate, and other fertilizers.

The following examples further illustrate the present invention, but, of course, should not be construed as in any way limiting its scope. The examples are organized to present protocols for the synthesis of the compounds of formula I of the present invention, set forth a list of such synthesized species, and set forth certain biological data indicating the efficacy of such compounds.

EXAMPLE 1

This example illustrates the preparation of 5-(3,3-Dichloroprop-2-enyloxy)-2-[4-(2,2-dimethyl(2,3-dihydrobenzo[2,3-b]furan-7-yloxy))butoxy]-1,3-dichlorobenzene (Compound 12 in table below)

Step A Synthesis of 1,3-Dichloro-2-(4-chlorobutoxy)-5-(phenylmethoxy)benzene as an Intermediate A stirred solution of 7.5 grams (0.028 mole) of 2,6-dichloro-4-phenylmethoxyphenol (known compound) and 3 mL (0.030 mole) of 1-bromo-4-chlorobutane in 225 mL of DMF was cooled in an ice bath, and 5.8 grams (0.042 mole) of potassium carbonate was added. Upon completion of addition, the reaction mixture was allowed to warm to ambient temperature as it stirred for about 18 hours. The reaction mixture was then poured into 1000 mL of an aqueous solution saturated with sodium chloride. The mixture was extracted with four 150 mL portions of diethyl ether, and the combined extracts were washed with 50 mL of water. The organic layer was dried with sodium sulfate, filtered, and concentrated under reduced pressure to a residue. The residue was purified with column chromatography on silica gel using 1:3 methylene chloride:hexane as an eluant. The appropriate fractions were combined and concentrated under reduced pressure, yielding 6.7 grams of the subject compound. The NMR spectrum was consistent with the proposed structure.

Step B Synthesis of 2-[4-(2,2-dimethyl(2,3-dihydrobenzo[2,3-b]faran-7-yloxy))butoxy]-1,3-dichloro-5-(phenylmethoxy)benzene as an Intermediate A stirred solution of 1.0 gram (0.0028 mole) of 1,3-dichloro-2-(4-chlorobutoxy)-5-(phenylmethoxy)benzene, 0.6 gram (0.0034 mole) of 2,2-dimethyl-2,3-dihydrobenzo[b]furan-7-ol (known compound), and 0.6 gram (0.0043 mole) of potassium carbonate in 25 mL of DMF was heated at 80° C. for about 18 hours. After this time, the reaction mixture was cooled and 50 mL of water was added. The mixture was then extracted with three 25 mL portions of diethyl ether. The combined extracts were washed with 25 mL of an aqueous solution saturated with sodium chloride. The organic layer was dried with sodium sulfate, filtered, and concentrated under reduced pressure to a residue. The residue was purified with column chromatography on silica gel using mixtures of 1:3 methylene chloride:hexane and 1:1 methylene chloride:hexane as eluants. The appropriate fractions were combined and concentrated under reduced pressure, yielding 0.87 gram of the subject compound. The NMR spectrum was consistent with the proposed structure.

Step C Synthesis of 4-[4-(2,2-dimethyl(2,3-dihydrobenzo[2,3-b]furan-7-yloxy))butoxy]-3,5-dichlorophenol as an Intermediate A mixture of 0.67 gram (0.0014 mole) of, 2-[4-(2,2-dimethyl(2,3-dihydrobenzo[2,3-b]furan-7-yloxy))butoxy]-1,3-dichloro-5-(phenylmethoxy)benzene and 0.01 gram (catalyst) of 10% palladium on carbon in 75 mL of methanol was subjected to hydrogenation conditions using a Parr Hydrogenator, yielding 0.55 gram of the subject compound. The NMR spectrum was consistent with the proposed structure.

Step D Synthesis of Compound 12

A stirred solution of 0.44 gram (0.0011 mole) of 4-[4-(2,2-dimethyl(2,3-dihydrobenzo[2,3-b]furan-7-yloxy))butoxy]-3,5-dichlorophenol, 0.3 gram (0.0015 mole) of 1,1,1,3-tetrachloropropane, and 0.3 gram (0.0022 mole) of potassium carbonate in 25 mL of DMF was heated at 80° C. for about 18 hours. After this time, the reaction mixture was cooled, and then it was poured into 50 mL of water. The mixture was saturated with solid sodium chloride and extracted with three 25 mL portions of diethyl ether. The combined extracts were washed with 25 mL of water and dried with sodium sulfate. The mixture was filtered, and the filtrate was concentrated under reduced pressure to a residue. The residue was purified with column chromatography on silica gel using 1:1 methylene chloride:hexane as an eluant. The appropriate fractions were combined and concentrated under reduced pressure, yielding 0.39 gram of compound 15. The NMR spectrum was consistent with the proposed structure.

EXAMPLE 2

This example illustrates the preparation of 7-{4-[4-(3,3-dichloroprop-2-enyloxy)-2,6-dichlorophenoxy]butoxy}2,2-dimethyl-2-hydrobenzo[b]furan-3-one (Compound 36 in table below)

A mixture of 0.20 gram (0.0004 mole) of Compound 12 (Prepared in Example 1), 0.26 gram (0.0010 mole) of potassium persulfate, and 0.10 gram (0.0004 mole) of copper sulfate pentasulfate in 15 mL of acetonitrile and 15 mL of water was stirred at 80° C. during a one hour period. After this time the reaction mixture was allowed to cool to ambient temperature, then it was extracted with two 15 mL portions of diethyl ether. The combined extracts were washed with one 15 mL portion of water, dried with sodium sulfate and filtered. The filtrate was concentrated under reduced pressure to a residual semi-solid. The semi-solid was purified with column chromatography on silica gel using methylene chloride as an eluant. The appropriate fractions were combined and concentrated under reduced pressure, yielding 0.03 gram of compound 36. The NMR spectrum was consistent with the proposed structure.

EXAMPLE 3

This example illustrates the preparation of 5-(3,3-dichloroprop-2-enyloxy)-2-{4-[2,2-dimethyl-5-(trifluoromethyl)(2,3-dihydrobenzo[2,3-b]furan-7-yloxy)]-butoxy}1,3-dichlorobenzene (Compound 20 in table below)

Step A Synthesis of 5-amino-2,2-dimethyl-2,3-dihydrobenzo[2,3-b]furan-7-yl acetate as an Intermediate A mixture of 3.5 grams (0.014 mole) of 2,2-dimethyl-5-nitro-2,3-dihydrobenzo[2,3-b]furan-7-yl acetate (known compound) and a catalytic amount of 10% palladium on carbon in 125 mL of ethanol was subjected to hydrogenation conditions using a Parr Hydrogenator. Upon completion of the uptake of the theoretical amount of hydrogen, the reaction mixture was filtered and concentrated under reduced pressure to a residue. The residue was purified with column chromatography on silica gel using methylene chloride, followed by 5% methanol in methylene chloride as eluants. The appropriate fractions were combined and concentrated under reduced pressure, yielding 2.7 grams of the subject compound. The NMR spectrum was consistent with the proposed structure.

Step B Synthesis of 5-iodo-2,2-dimethyl-2,3-dihydrobenzo[2,3-b]furan-7-yl acetate as an Intermediate A stirred solution of 1.0 gram (0.0045 mole) of 5-amino-2,2-dimethyl-2,3-dihydrobenzo[2,3-b]furan-7-yl acetate in 40 mL of acetonitrile was cooled in an ice-bath and 0.55 mL (0.0045 mole) of tert-butyl nitrite was added. Upon completion of addition, the reaction mixture was stirred for an additional 15 minutes with continued cooling. After this time 1.2 grams (0.0045 mole) of iodine was added in two portions during a five-minute period. Upon completion of addition, the reaction mixture was stirred for an additional one hour with continued cooling, allowed to warm to ambient temperature where it stirred for three hours, and then it was warmed to reflux where it stirred for 30 minutes. After this time the reaction mixture was cooled and poured into 50 mL of aqueous 10% hydrochloric acid and the mixture was extracted with two 25 mL portions of methylene chloride. The combined extracts were washed with one 25 mL portion of an aqueous solution saturated with sodium chloride, dried with sodium sulfate, and filtered. The filtrate was concentrated under reduced pressure to a residue. The residue was purified with column chromatography on silica gel using methylene chloride as an eluant. The appropriate fractions were combined and concentrated under reduced pressure, yielding 0.78 gram of the subject compound. The NMR spectrum was consistent with the proposed structure. The reaction was repeated to obtain additional intermediate.

Step C Synthesis of 2,2-dimethyl-5-(trifluoromethyl)-2,3-dihydro[2,3-b]furan-7-yl acetate as an Intermediate A stirred mixture of 1.2 grams (0.0037 mole) of 5-iodo-2,2-dimethyl-2,3-dihydrobenzo[2,3-b]furan-7-yl acetate, 1.5 grams (0.0074 mole) of methyl 2,2-difluoro-2-fluorosulfonyl acetate and 0.2 gram (0.001 mole) of copper iodide in 50 mL of DMF was heated at 80° C. during a six-hour period. A GC analysis of the reaction mixture after this time indicated that the reaction was about 70% complete. An additional 0.5 gram of methyl 2,2-difluoro-2-fluorosulfonyl acetate and 0.1 gram of copper iodide were added to the reaction mixture, and the heating at 80° C. was continued for an additional 18 hour period. The reaction mixture was allowed to cool to ambient temperature and then it was poured into 75 mL of water and extracted with three 25 mL portions of diethyl ether. The combined extracts were washed with two 25 mL portions of water, dried with sodium sulfate, and filtered. The filtrate was concentrated under reduced pressure to a residue. The residue was purified with column chromatography on silica gel using a mixture of 1:1 methylene chloride and hexane as an eluant. The appropriate fractions were combined and concentrated under reduced pressure, yielding 0.60 gram of the subject compound. The NMR spectrum was consistent with the proposed structure.

Step D Synthesis of 2,2-dimethyl-5-(trifluoromethyl)-2,3-dihydro[2,3-b]furan-7-ol as an Intermediate A solution of 0.6 gram (0.0022 mole) of 2,2-dimethyl-5-(trifluoromethyl)-2,3-dihydro[2,3-b]furan-7-yl acetate in 5 mL of methanol was stirred and a solution of 0.9 gram (0.0220 mole) of sodium hydroxide in 15 mL of water was added. Upon completion of addition the reaction mixture was warmed to 40° C. where it stirred for two hours. After this time the reaction mixture was allowed to cool to ambient temperature as it stirred during an 18 hour period. The reaction mixture was then acidified to a pH of 6 using concentrated hydrochloric acid and then it was extracted with three 25 mL portions of diethyl ether. The combined extracts were washed with one 25 mL portion of water, dried with sodium sulfate, and filtered. The filtrated was concentrated under reduced pressure, yielding 0.4 gram of the subject compound. The NMR spectrum was consistent with the proposed structure.

Step E Synthesis of 4-[2,6-dichloro-4-(phenylmethoxy)phenoxy]butan-1-ol as an Intermediate A solution of 33.9 grams (0.126 mole) of 2,6-dichloro-4-phenylmethoxyphenol (known compound), 16.4 grams (0.151 mole) of 4-chlorobutan-1-ol and 20.9 grams (0.151 mole) of potassium carbonate in 300 mL of DMF was warmed to 80° C. where it stirred during an 18 hour period. After this time the reaction mixture was concentrated under reduced pressure to a residue. Water was added to the residue and the mixture was extracted with ethyl acetate. The extract was washed with water and then with an aqueous solution saturated with sodium chloride. The organic layer was dried with magnesium sulfate and filtered, and the filtrate was concentrated under reduced pressure to a residue. The residue was purified with column chromatography on silica gel using a mixture of 1:1 ethyl acetate and hexane as an eluant. The appropriate fractions were combined and concentrated under reduced pressure, yielding 12.2 grams of the subject compound. The NMR spectrum was consistent with the proposed structure.

Step F Synthesis of 3,5-dichloro-4-(4-hydroxybutoxy)phenol as an Intermediate

This compound was prepared in a manner analogous to that of Step A of this example, using 12.2 grams (0.036 mole) of 4-[2,6-dichloro-4-(phenylmethoxy)phenoxy]butan-1-ol and 0.5 gram (catalyst) of 10% palladium on carbon and a theoretical amount of hydrogen gas in a Parr Hydrogenator. The yield of the subject compound was 9.3 grams. The NMR spectrum was consistent with the proposed structure.

Step G Synthesis of 4-[4-(3,3-dichloroprop-2-enyloxy)-2,6-dichlorophenoxy]butan-1-ol as an Intermediate This compound was prepared in a manner analogous to that of Step D of Example 1, using 9.3 grams (0.036 mole) of 3,5-dichloro-4-(4-hydroxybutoxy)phenol, 7.7 grams (0.042 mole) of 1,1,1,3-tetrachloropropane and 11.7 grams (0.080 mole) of potassium carbonate in 300 mL of DMF. The crude product was purified with column chromatography on silica gel using mixtures of 1:4 and 1:1 ethyl acetate and hexane as eluants. The appropriate fractions were combined and concentrated under reduced pressure, yielding 8.0 grams of the subject compound. The NMR spectrum was consistent with the proposed structure.

Step H Synthesis of 1-[4-(3,3-dichloroprop-2-enyloxy)-2,6-dichlorophenoxy]-4-bromobutane as an Intermediate A stirred solution of 7.3 grams (0.020 mole) of 4-[4-(3,3-dichloroprop-2-enyloxy)-2,6-dichlorophenoxy]butan-1-ol in 400 mL of methylene chloride was cooled in an ice bath and, in turn, 5.5 grams (0.021 mole) of triphenylphosphine and 6.9 grams (0.021 mole) of carbon tetrabromide were added. Upon completion of addition the reaction mixture was stirred with continued cooling for one hour, then it was allowed to warm to ambient temperature where it stirred during an 18-hour period. After this time the reaction mixture was concentrated under reduced pressure to a residue. The residue was purified with column chromatography on silica gel using hexane and a mixture of 1:1 methylene chloride and heptane as an eluant. The appropriate fractions were combined and concentrated under reduced pressure, yielding 12.2 grams of the subject compound. The NMR spectrum was consistent with the proposed structure.

Step I Synthesis of Compound 20

Under a nitrogen atmosphere, a solution of 0.18 gram (0.0004) mole of 1-[4-(3,3-dichloroprop-2-enyloxy)-2,6-dichlorophenoxy]-4-bromobutane, 0.10 gram (0.0004 mole) of 2,2-dimethyl-5-(trifluoromethyl)-2,3-dihydro[2,3-b]furan-7-ol (prepared in Step D of this example) and 0.09 gram (0.0007 mole) of potassium carbonate in 15 mL of DMF was stirred at ambient temperature during an 18-hour period. After this time the reaction mixture was stirred with 25 mL of water and was saturated with solid sodium chloride. The mixture was then extracted with two 25 mL portions of diethyl ether; and the combined extracts were washed with one 25 mL portion of water, dried with sodium sulfate, filtered and concentrated under reduced pressure to a residue. The residue was purified with column chromatography on silica gel using hexane and a mixture of 1:1 methylene chloride and hexane as eluants. The appropriate fractions were combined and concentrated under reduced pressure, yielding 0.19 gram of compound 20. The NMR spectrum was consistent with the proposed structure.

EXAMPLE 4

This example illustrates the preparation of N-{3-[4-(3,3-dichloroprop-2-enyloxy)-2,6-dichlorophenoxy]propyl}(2,2-dimethyl(2,3-dihydrobenzo[2,3-b]furan-7-yloxy))-carboxamide (Compound 53 in table below)

Step A Synthesis of 2,2-dimethyl-2,3-dihydrobenzo[2,3-b] benzofuran-7-yl imidazolecarboxylate as an Intermediate A solution of 1.64 grams (0.010 mole) of 2,2-dimethyl-2,3-dihydrobenzo[b]furan-7-ol (known compound) in 30 mL of methylene chloride was stirred, and 1.62 grams (0.010 mole) of 1,1'-carbonyldiimidazole was added in one portion. Upon completion of addition the reaction mixture was stirred at ambient temperature for 20 minutes. After this time the reaction mixture was concentrated under reduced pressure to a residue. The residue was dissolved in a mixture of 1:1 methylene chloride and hexanes and purified by column chromatography on silica gel using a mixture of 7:4 hexane and ethyl acetate as an eluant. The appropriate fractions were combined and concentrated under reduced pressure, yielding 1.96 grams of the subject compound. The NMR spectrum was consistent with the proposed structure.

Step B Synthesis of N-{3-[2,6-dichloro-4-(phenylmethoxy) phenoxy]propyl}(tert.-butoxy)carboxamide as an Intermediate A solution of 2.69 grams (0.010 mole) of 2,6-dichloro-4-phenylmethoxyphenol (known compound), 2.38 grams (0.010 mole) of (tert-butoxy)-N-(3-bromopropyl)carboxamide (commercially available) and 1.52 grams (0.011 mole) of potassium carbonate in 40 mL of DMF was stirred at ambient temperature during a four-day period. After this time the reaction mixture was shaken in diethyl ether and water, and the separated organic layer was washed with one portion of water and with one portion of an aqueous solution saturated with sodium chloride. The organic layer was dried with sodium sulfate and filtered. The filtrate was concentrated under reduced pressure, yielding 4.15 grams of the subject compound.

Step C Synthesis of N-[3-(2,6-dichloro-4-hydroxyphenoxy)propyl](tert-butoxy)carboxamide as an Intermediate This compound was prepared in a manner analogous to that of Step A of Example 3, using 4.1 grams (0.0096 mole) of N-{3-[2,6-dichloro-4-(phenylmethoxy)phenoxy]propyl}(tert.-butoxy)carboxamide, a catalytic amount of 10% palladium on carbon and a theoretical amount of hydrogen gas in 60 mL of 1:1 ethanol and ethyl acetate in a Parr Hydrogenator. The yield of the subject compound was 3.5 grams.

Step D Synthesis of N-{3-[4-(3,3-dichloroprop-2-enyloxy)-2,6-dichlorophenoxy]propyl}(tert-butoxy)carboxamide as an Intermediate This compound was prepared in a manner analogous to that of Step D of Example 1, using 3.5 grams (0.0104 mole) of N-[3-(2,6-dichloro-4-hydroxyphenoxy)propyl](tert-butoxy)carboxamide, 2.3 grams (0.0125 mole) of 1,1,1,3-tetrachloropropane and 3.4 grams (0.0250 mole) of potassium carbonate in DMF. The crude product was purified with column chromatography on silica gel using a mixture of 1:3 hexane and methylene chloride as an eluant. The appropriate fractions were combined and concentrated under reduced pressure, yielding 2.6 grams of the subject compound. The NMR spectrum was consistent with the proposed structure.

Step E Synthesis of 3-[4-(3,3-dichloroprop-2-enyloxy)-2,6-dichlorophenoxy]propylamine hydrochloride as an Intermediate A stirred solution of 2.6 grams (0.0058 mole) of N-{3-[4-(3,3-dichloroprop-2-enyloxy)-2,6-dichlorophenoxy]propyl}(tert-butoxy)carboxamide in 10 mL of anhydrous diethyl ether was cooled to 0° C. and a 2N solution of hydrogen chloride in diethyl ether was added via a syringe. Upon completion of addition the reaction mixture was allowed to warm to ambient temperature where it stirred during an 18-hour period. A resultant solid precipitate was collected by filtration, yielding when dried, 1.25 grams of the subject compound. The filtrate was taken up in hexanes and allowed to stand during an 18-hour period, during which time a second crop of the subject compound precipitated from the filtrate. The precipitate was collected by filtration and dried, yielding an additional 0.83 gram of the subject compound.

Step F Synthesis of Compound 53

A solution of 82 milligrams (0.318 mmole) of 2,2-dimethyl-2,3-dihydrobenzo[2,3-b]benzofuran-7-yl imidazolecarboxylate (prepared in Step A of this example), 100 milligrams (0.262 mmole) of 3-[4-(3,3-dichloroprop-2-enyloxy)-2,6-dichlorophenoxy]propylamine hydrochloride and 73 microliters (0.524 mmole) of triethylamine in five mL of methylene chloride was stirred at ambient temperature during an 18-hour period. After this time TLC analysis of the reaction mixture indicated that no reaction had taken place. The reaction mixture was concentrated under reduced pressure to remove the methylene chloride, and five mL of acetonitrile was added. The reaction mixture was then heated at reflux during an 18-hour period after which time TLC analysis indicated that the reaction had taken place, albeit incomplete. The reaction mixture was then concentrated under reduced pressure to a residue. The residue was dissolved in a mixture of 1:1 dichloromehane and hexanes and purified by column chromatography on silica gel using a mixture of 4:1 hexane and ethyl acetate as an eluant. The appropriate fractions were combined and concentrated under reduced pressure, yielding 45 milligrams of compound 53. The NMR spectrum was consistent with the proposed structure.

It is well known to one of ordinary skill in the art that compounds like the compounds of formula I of the present invention can contain optically active and racemic forms. It is also well known in the art that compounds like the compounds of formula I may contain stereoisomeric forms, tautomeric forms and/or exhibit polymorphism. It is to be understood that the present invention encompasses any racemic, optically active, polymorphic, tautomeric, or stereoisomeric form, or mixtures thereof. It should be noted that it is well known in the art how to prepare optically active forms, for example by resolution of a racemic mixture, or by synthesis from optically active intermediates.

The following table sets forth examples of compounds of formula I:

TABLE 1

Insecticidal (dihalopropenyl) phenylalkyl substituted dihydrobenzofuran and dihydrobenzopyran derivatives

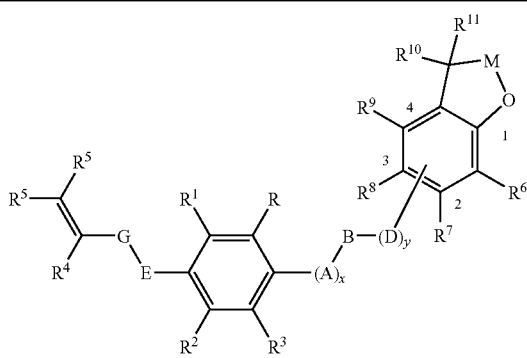

where B is a bridging group of the formula:
—(CR$^{16}$R$^{17}$)$_q$—(CR$^{18}$R$^{19}$)$_r$—(CR$^{20}$R$^{21}$)$_s$—L$_t$—(CR$^{22}$R$^{23}$)$_u$—(CR$^{24}$R$^{25}$)$_v$—(CR$^{26}$R$^{27}$)$_w$—
where R$^1$, R$^2$, R$^4$, R$^{10}$ and R$^{11}$ are hydrogen; R, R$^3$ and R$^5$'s are chloro; M is —C(R$^{32}$R$^{33}$)—, where R$^{32}$ and R$^{33}$ are methyl; q and r are 1, where R$^{16}$, R$^{17}$, R$^{18}$ and R$^{19}$ are hydrogen; s, t, u, v and w are 0; x and y are 1; A, D and E are O, and G is (CH$_2$)$_n$ where n is 1; providing compounds of formula IA as set forth below:

TABLE 1-continued

Insecticidal (dihalopropenyl) phenylalkyl substituted dihydrobenzofuran and dihydrobenzopyran derivatives

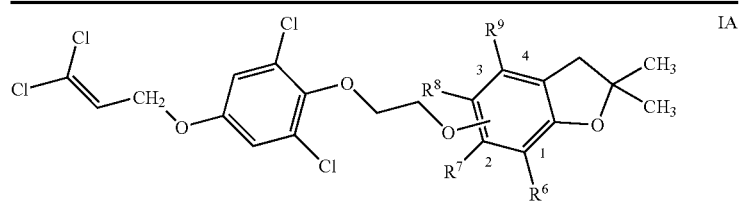

IA

| Cmpd. No. | Point of attachment of D to Benzo-fused ring | $R^6$ | $R^7$ | $R^8$ | $R^9$ |
|---|---|---|---|---|---|
| 1 | 1 | — | H | Cl | H | where $R^1$, $R^2$, $R^4$, $R^{10}$ and $R^{11}$ are hydrogen; R, $R^3$ and $R^5$'s are chloro; M is —C($R^{32}R^{33}$)—, where $R^{32}$ and $R^{33}$ are methyl; q, r and s are 1, where $R^{16}$, $R^{17}$, $R^{18}$, $R^{19}$ and $R^{21}$ are hydrogen, and unless otherwise noted $R^{20}$ is hydrogen; t, u, v and w are 0; x and y are 1; A, D and E are O, and G is $(CH_2)_n$ where n is 1; providing compounds of formula 1B as set forth below:

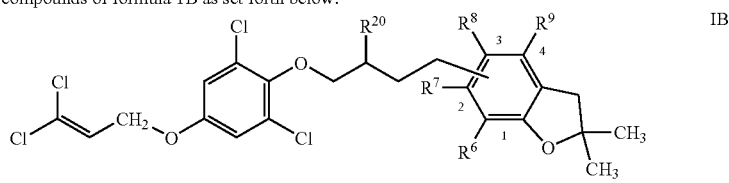

IB

| Cmpd. No. | Point of attachment of D to Benzo-fused ring | $R^6$ | $R^7$ | $R^8$ | $R^9$ |
|---|---|---|---|---|---|
| 2 | 1 | — | H | H | H |
| 3 | 1 | — | H | H | Cl |
| 4 | 1 | — | H | Cl | H |
| 5* | 1 | — | H | Cl | H |
| 6 | 1 | — | H | Br | H |
| 7 | 1 | — | H | $NO_2$ | H |
| 9 | 1 | — | H | $NHCO_2C_2H_5$ | H |

*$R^{20}$ is methyl.

where $R^2$, $R^4$, $R^{10}$ and $R^{11}$ are hydrogen; R and $R^5$'s are chloro; M is —C($R^{32}R^{33}$)—, where $R^{32}$ and $R^{33}$ are methyl; q, r, s and u are 1, where $R^{16}$, $R^{17}$, $R^{18}$, $R^{19}$ $R^{20}$, $R^{21}$, $R^{22}$ and $R^{23}$ are hydrogen, t, v and w are 0; x and y are 1; A, D and E are O, and G is $(CH_2)_n$ where n is 1; providing compounds of formula IC as set forth below:

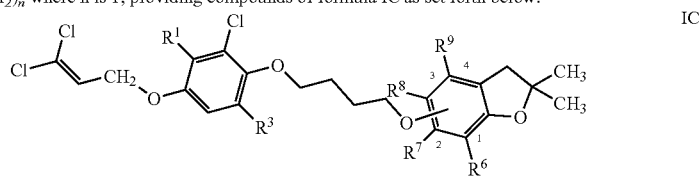

IC

| Cmpd. No. | $R^1$ | $R^3$ | Point of attachment of D to Benzo-fused ring | $R^6$ | $R^7$ | $R^8$ | $R^9$ |
|---|---|---|---|---|---|---|---|
| 10 | H | H | 1 | — | H | H | H |
| 11 | H | Cl | 4 | H | H | H | — |
| 12 | H | Cl | 1 | — | H | H | H |
| 13 | Cl | Cl | 1 | — | H | H | H |
| 14 | H | Cl | 4 | Cl | H | H | — |
| 15 | H | Cl | 1 | — | H | H | Cl |
| 16 | H | Cl | 1 | — | H | Cl | H |
| 17 | H | Cl | 1 | — | H | H | Br |
| 18 | H | Cl | 1 | — | H | Br | H |
| 19 | H | Cl | 1 | — | H | I | H |
| 20 | H | Cl | 1 | — | H | $CF_3$ | H |
| 21 | H | Cl | 1 | — | H | C≡N | H |
| 22 | H | Cl | 1 | — | H | $NO_2$ | H |
| 23 | H | Cl | 1 | — | $NO_2$ | H | $CH_3$ |
| 24 | H | Cl | 1 | — | H | $NH_2$ | H |
| 25 | H | Cl | 1 | — | H | NHC(=O)$CH_3$ | H |
| 26 | H | Cl | 1 | — | H | NHC(=O)Ph | H |
| 27 | H | Cl | 1 | — | H | $NHCO_2C_2H_5$ | H |

TABLE 1-continued

Insecticidal (dihalopropenyl) phenylalkyl substituted dihydrobenzofuran and dihydrobenzopyran derivatives

| | | | | | | | | |
|---|---|---|---|---|---|---|---|---|
| 28 | H | Cl | 1 | — | H | Ph | H | | where $R^1$, $R^2$, $R^4$ and $R^{11}$ are hydrogen; R, $R^3$ and $R^5$'s are chloro; M is —C($R^{32}R^{33}$)—, where $R^{32}$ and $R^{33}$ are methyl; q, r, s and u are 1, where $R^{16}$, $R^{17}$, $R^{18}$, $R^{19}$ $R^{20}$, $R^{21}$, $R^{22}$ and $R^{23}$ are hydrogen, t, v and w are 0; x and y are 1; A, D and E are O, and G is $(CH_2)_n$ where n is 1; providing compounds of formula ID as set forth below:

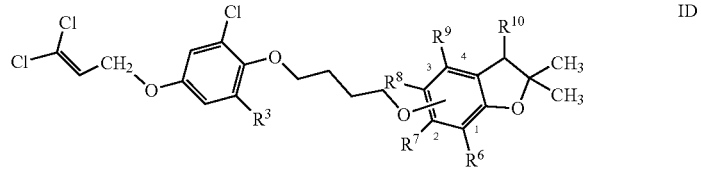

ID

| Cmpd. No. | Point of attachment of D to Benzo-fused ring | $R^6$ | $R^7$ | $R^8$ | $R^9$ | $R^{10}$ |
|---|---|---|---|---|---|---|
| 29 | 1 | — | H | H | H | F |
| 30 | 1 | — | H | H | H | OH | where $R^1$, $R^2$, $R^4$, $R^{10}$ and $R^{11}$ are hydrogen; R, $R^3$ and $R^5$'s are chloro; M is —C($R^{32}R^{33}$)—, where $R^{32}$ and $R^{33}$ are methyl; q, r, s and u are 1, where $R^{16}$, $R^{17}$, $R^{18}$, $R^{19}$ $R^{20}$, $R^{21}$, $R^{22}$ and $R^{23}$ are hydrogen, t, v and w are 0; x and y are 1; A and E are O, D is $NR^{15}$ and G is $(CH_2)_n$ where n is 1; providing compounds of formula IE as set forth below:

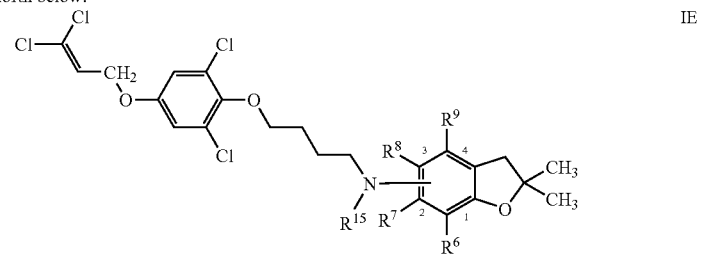

IE

| Cmpd. No. | Point of attachment of D to Benzo-fused ring | $R^6$ | $R^7$ | $R^8$ | $R^9$ | $R^{15}$ |
|---|---|---|---|---|---|---|
| 31 | 1 | — | H | H | H | $CH_2CH=C(Cl)_2$ |
| 32 | 1 | — | H | H | H | $C(=O)CH_3$ | where $R^1$, $R^2$, and $R^4$ are hydrogen; R, $R^3$ and $R^5$'s are chloro; M is —C($R^{32}R^{33}$)—; q, r, s and u are 1, where $R^{16}$, $R^{17}$, $R^{18}$, $R^{19}$ $R^{20}$, $R^{21}$, $R^{22}$ and $R^{23}$ are hydrogen, t, v and w are 0; x and y are 1; A, D and E are O, and G is $(CH_2)_n$ where n is 1; providing compounds of formula IF as set forth below:

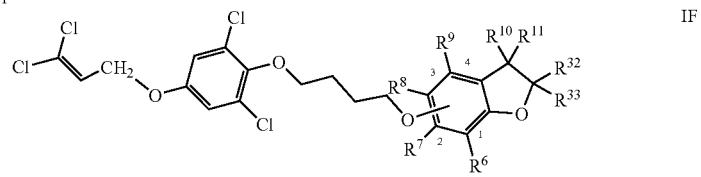

IF

| Cmpd. No. | Point of attachment of D to Benzo fused ring | $R^6$ | $R^7$ | $R^8$ | $R^9$ | $R^{10}$ | $R^{11}$ | $R^{32}$ | $R^{33}$ |
|---|---|---|---|---|---|---|---|---|---|
| 33 | 1 | — | H | H | H | F | F | F | F | where $R^1$, $R^2$ and $R^4$ are hydrogen; R, $R^3$ and $R^5$'s are chloro; $R^{10}$ and $R^{11}$ are taken together with —$SCH_2CH_2S$—to form a thioketal; M is —C($R^{32}R^{33}$)—, where $R^{32}$ and $R^{33}$ are methyl; q, r, s and u are 1, where $R^{16}$, $R^{17}$, $R^{18}$, $R^{19}$ $R^{20}$, $R^{21}$, $R^{22}$ and $R^{23}$ are hydrogen, t, v and w are 0; x and y are 1; A, D and E are O, and G is $(CH_2)_n$ where n is 1; providing compounds of formula IG as set forth below:

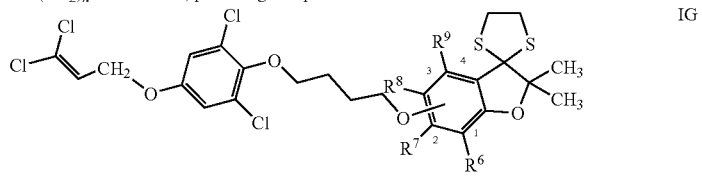

IG

TABLE 1-continued

Insecticidal (dihalopropenyl) phenylalkyl substituted dihydrobenzofuran and dihydrobenzopyran derivatives

| Cmpd. No. | $R^1$ | $R^3$ | Point of attachment of D to Benzo-fused ring | $R^6$ | $R^7$ | $R^8$ | $R^9$ |
|---|---|---|---|---|---|---|---|
| 34 | H | H | 1 | — | H | H | H | where $R^1$, $R^2$, and $R^4$ are hydrogen; R, $R^3$ and $R^5$'s are chloro; $R^{10}$ and $R^{11}$ are taken together with O to form a carbonyl group; M is —C($R^{32}R^{33}$)—, where $R^{32}$ and $R^{33}$ are methyl; q, r and s are 1, where $R^{16}$, $R^{17}$, $R^{18}$, $R^{19}$ and $R^{21}$ are hydrogen; t and w are 0; x and y are 1; u and v are 0 or 1 and when u and v are 1, $R^{22}$, $R^{23}$, $R^{24}$ and $R^{25}$ are hydrogen; A, D and E are O, and G is (CH$_2$)$_n$ where n is 1; and the benzo-fused ring is attached at the 1-position, providing compounds of formula IH as set forth below:

IH

| Cmpd. No | u | v | $R^7$ | $R^8$ | $R^9$ |
|---|---|---|---|---|---|
| 35 | 0 | 0 | H | H | H |
| 36 | 1 | 0 | H | H | H |
| 37 | 1 | 0 | H | H | Cl |
| 38 | 1 | 0 | H | Cl | H |
| 39 | 1 | 0 | Cl | H | Cl |
| 40 | 1 | 1 | Cl | H | Cl | where $R^1$, $R^2$, $R^4$, $R^{10}$ and $R^{11}$ are hydrogen; R, $R^3$ and $R^5$'s are chloro; M is —C($R^{32}R^{33}$)—, where $R^{32}$ and $R^{33}$ are methyl; q, r, s, u and v are 1, where $R^{16}$, $R^{17}$, $R^{18}$, $R^{19}$ $R^{20}$, $R^{21}$, $R^{22}$, $R^{23}$, $R^{24}$ and $R^{25}$ are hydrogen, t and w are 0; x and y are 1; A, D and E are O, and G is (CH$_2$)$_n$ where n is 1; providing compounds of formula II as set forth below:

II

| Cmpd. No. | Point of attachment of D to Benzo-fused ring | $R^6$ | $R^7$ | $R^8$ | $R^9$ |
|---|---|---|---|---|---|
| 41 | 1 | — | H | H | H |
| 42 | 1 | — | H | Cl | H |
| 43 | 1 | — | H | Br | H |
| 44 | 1 | — | H | CF3 | H | where $R^1$, $R^2$, $R^4$, $R^{10}$ and $R^{11}$ are hydrogen; R, $R^3$ and $R^5$'s are chloro; M is —C($R^{32}R^{33}$)—, where $R^{32}$ and $R^{33}$ are methyl; q, r, s, u and v are 1, where $R^{16}$, $R^{17}$, $R^{18}$, $R^{19}$ $R^{20}$, $R^{21}$, $R^{22}$, $R^{23}$, $R^{24}$ and $R^{25}$ are hydrogen, t and w are 0; x and y are 1; A and E are O, and G is (CH$_2$)$_n$ where n is 1; and D is NR$^{15}$ providing compounds of formula IJ as set forth below:

IJ

TABLE 1-continued

Insecticidal (dihalopropenyl) phenylalkyl substituted dihydrobenzofuran and dihydrobenzopyran derivatives

| Cmpd. No. | Point of attachment of D to Benzo-fused ring | $R^6$ | $R^7$ | $R^8$ | $R^9$ | $R^{15}$ |
|---|---|---|---|---|---|---|
| 45 | 1 | — | H | H | H | H |
| 46 | 1 | — | H | H | H | $CH_3$ |
| 47 | 1 | — | H | H | H | $CH_2C\!\!=\!\!CH_2$ |
| 48 | 1 | — | H | H | H | $CH_2Ph$ | where $R^1$, $R^2$, $R^4$, $R^{10}$ and $R^{11}$ are hydrogen; R, $R^3$ and $R^5$'s are chloro; M is —C($R^{32}R^{33}$)—, where $R^{32}$ and $R^{33}$ are methyl; q, r, u and v are 1, where $R^{16}$, $R^{17}$, $R^{18}$, $R^{19}$, $R^{22}$, $R^{23}$, $R^{24}$ and $R^{25}$ are hydrogen, t is 1; s and w are 0; x and y are 1; A, D, E and L are O, and G is $(CH_2)_n$ where n is 1; providing compounds of formula IK as set forth below:

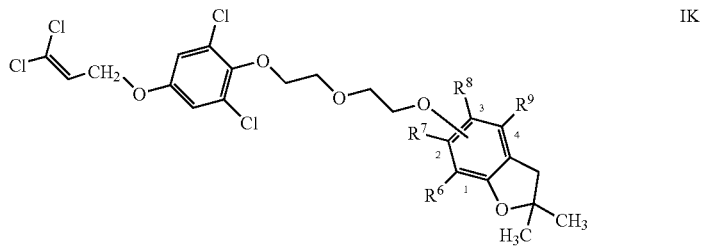

IK

| Cmpd. No. | Point of attachment of D to Benzo-fused ring | $R^6$ | $R^7$ | $R^8$ | $R^9$ |
|---|---|---|---|---|---|
| 49 | 1 | — | H | H | H |
| 50 | 1 | — | H | Cl | H | where $R^1$, $R^2$, $R^4$, $R^{10}$ and $R^{11}$ are hydrogen; R, $R^3$ and $R^5$'s are chloro; M is —C($R^{32}R^{33}$)—, where $R^{32}$ and $R^{33}$ are methyl; q, r, s, u, v and w are 1, where $R^{16}$ $R^{17}$, $R^{18}$ $R^{19}$ $R^{20}$, $R^{21}$, $R^{22}$, $R^{23}$ $R^{24}$ $R^{25}$, $R^{26}$ and $R^{27}$ are hydrogen, t is 0; x and y are 1; A, D and E are O, and G is $(CH_2)_n$ where n is 1; providing compounds of formula IL as set forth below:

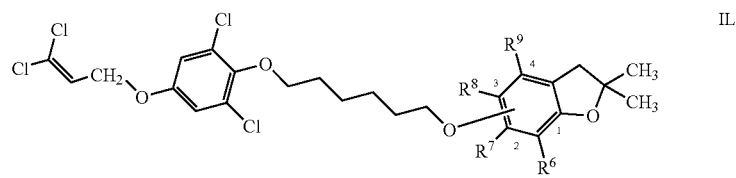

IL

| Cmpd. No. | Point of attachment of D to Benzo-fused ring | $R^6$ | $R^7$ | $R^8$ | $R^9$ |
|---|---|---|---|---|---|
| 51 | 1 | — | H | H | H | where $R^1$, $R^2$, $R^4$, $R^{10}$ and $R^{11}$ are hydrogen; R, $R^3$ and $R^5$'s are chloro; M is —C($R^{32}R^{33}$)—, where $R^{32}$ and $R^{33}$ are methyl; q, r s and t are 1, where $R^{16}$, $R^{17}$, $R^{18}$, $R^{19}$ $R^{20}$, and $R^{21}$ are hydrogen and L is OC(=O), u, v and w are 0; x and y are 1; A and E are O; D is $NR^{15}$ where $R^{15}$ is hydrogen; and G is $(CH_2)_n$ where n is 1; providing compounds of formula IM as set forth below:

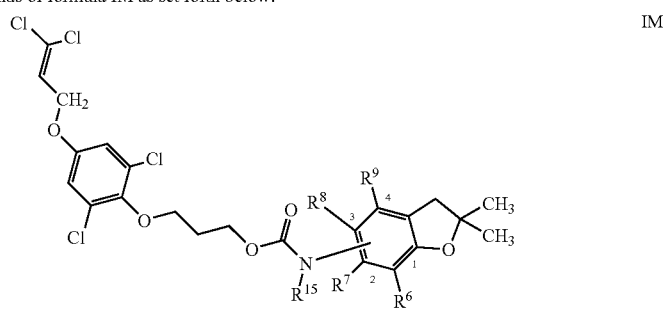

IM

TABLE 1-continued

Insecticidal (dihalopropenyl) phenylalkyl substituted dihydrobenzofuran and dihydrobenzopyran derivatives

| Cmpd. No. | Point of attachment of D to Benzo-fused ring | $R^6$ | $R^7$ | $R^8$ | $R^9$ |
|---|---|---|---|---|---|
| 52 | 1 | — | H | H | H | where $R^1$, $R^2$, $R^4$, $R^{10}$ and $R^{11}$ are hydrogen; R, $R^3$ and $R^5$'s are chloro; M is —$C(R^{32}R^{33})$—, where $R^{32}$ and $R^{33}$ are methyl; q, r s and t are 1, where $R^{16}$, $R^{17}$, $R^{18}$, $R^{19}$ $R^{20}$, and $R^{21}$ are hydrogen and L is NHC(=O), u, v and w are 0; x and y are 1; A, D and E are O, and G is $(CH_2)_n$ where n is 1; providing compounds of formula IN as set forth below:

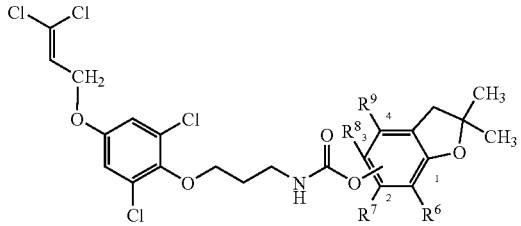

IN

| Cmpd. No. | Point of attachment of D to Benzo-fused ring | $R^6$ | $R^7$ | $R^8$ | $R^9$ |
|---|---|---|---|---|---|
| 53 | 1 | — | H | H | H | where $R^1$, $R^2$, $R^4$, $R^{10}$, and $R^{11}$ are hydrogen; R, $R^3$ and $R^5$'s are chloro; M is —$C(R^{32}R^{33})C(R^{34}R^{35})$—, where $R^{32}$ and $R^{33}$ are hydrogen and $R^{34}$ and $R^{35}$ are methyl; q, r, s and u are 1, where $R^{16}$, $R^{17}$, $R^{18}$, $R^{19}$ $R^{20}$, $R^{21}$, $R^{22}$ and $R^{23}$ are hydrogen, t, v and w are 0; x and y are 1; A, D and E are O, and G is $(CH2)_n$ where n is 1; providing compounds of formula IO as set forth below:

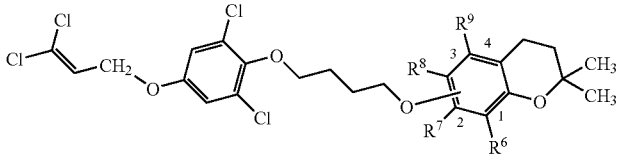

IO

| Cmpd. No. | Point of attachment of D to Benzo-fused ring | $R^6$ | $R^7$ | $R^8$ | $R^9$ |
|---|---|---|---|---|---|
| 54 | 1 | — | H | H | Cl |

TABLE 2

Insecticidal (dihalopropenyl) phenylalkyl substituted dihydrobenzofuran and dihydrobenzopyran derivatives Characterizing Data

| Cmpd. No. | Emperical Formulae | Physical State | Cmpd. No. | Emperical Formulae | Physical State |
|---|---|---|---|---|---|
| 1 | $C_{21}H_{19}Cl_5O_4$ | Solid | 2 | $C_{22}H_{22}Cl_4O_4$ | Liquid |
| 3 | $C_{22}H_{21}Cl_5O_4$ | Liquid | 4 | $C_{22}H_{21}Cl_5O_4$ | Solid, 86-90° C. |
| 5 | $C_{23}H_{23}Cl_5O_4$ | Oil | 6 | $C_{22}H_{21}BrCl_4O_4$ | Solid, 64-68° C. |
| 7 | $C_{23}H_{21}Cl_4NO_4$ | Solid, 88-93° C. | | | |
| 9 | $C_{25}H_{27}Cl_4NO_6$ | Solid, 106-110° C. | 10 | $C_{23}H_{25}Cl_3O_4$ | Solid, 68-70° C. |
| 11 | $C_{23}H_{24}Cl_4O_4$ | Oil | 12 | $C_{23}H_{24}Cl_4O_4$ | Liquid |
| 13 | $C_{23}H_{23}Cl_5O_4$ | Liquid | 14 | $C_{23}H_{23}Cl_5O_4$ | Oil |
| 15 | $C_{23}H_{23}Cl_5O_4$ | Liquid | 16 | $C_{23}H_{23}Cl_5O_4$ | Solid, 56-60° C. |
| 17 | $C_{23}H_{23}BrCl_4O_4$ | Semi-solid | 18 | $C_{23}H_{23}BrCl_4O_4$ | Liquid |
| 19 | $C_{23}H_{23}Cl_4IO_4$ | Liquid | 20 | $C_{24}H_{23}Cl_4F_3O_4$ | Liquid |
| 21 | $C_{24}H_{23}Cl_4NO_4$ | Solid, 89-95° C. | 22 | $C_{23}H_{23}Cl_4NO_6$ | Solid, 101-104° C. |
| 23 | $C_{24}H_{25}Cl_4NO_6$ | Solid, 72-75° C. | 24 | $C_{23}H_{25}Cl_4NO_4$ | Liquid |
| 25 | $C_{25}H_{27}Cl_4NO_5$ | Liquid | 26 | $C_{30}H_{29}Cl_4NO_5$ | Liquid |
| 27 | $C_{26}H_{29}Cl_4NO_6$ | Liquid | 28 | $C_{29}H_{28}Cl_4O_4$ | Liquid |
| 29 | $C_{23}H_{23}Cl_4FO_4$ | Liquid | 30 | $C_{23}H_{24}Cl_4O_5$ | Liquid |
| 31 | $C_{26}H_{27}Cl_6NO_3$ | Oil | 32 | $C_{25}H_{27}Cl_4NO_4$ | Oil |
| 33 | $C_{21}H_{16}Cl_4F_4O_4$ | Liquid | 34 | $C_{25}H_{26}Cl_4O_4S_2$ | Liquid |
| 35 | $C_{22}H_{20}Cl_4O_5$ | Liquid | 36 | $C_{23}H_{22}Cl_4O_5$ | Liquid |
| 37 | $C_{23}H_{21}Cl_5O_5$ | Liquid | 38 | $C_{23}H_{21}Cl_5O_5$ | Liquid |
| 39 | $C_{23}H_{20}Cl_6O_5$ | Oil | 40 | $C_{24}H_{22}Cl_6O_5$ | Oil |
| 41 | $C_{24}H_{26}Cl_4O_4$ | Liquid | 42 | $C_{24}H_{25}Cl_5O_4$ | Liquid |

TABLE 2-continued

Insecticidal (dihalopropenyl) phenylalkyl substituted dihydrobenzofuran and dihydrobenzopyran derivatives Characterizing Data

| Cmpd. No. | Emperical Formulae | Physical State | Cmpd. No. | Emperical Formulae | Physical State |
|---|---|---|---|---|---|
| 43 | $C_{24}H_{25}BrCl_4O_4$ | Liquid | 44 | $C_{25}H_{25}Cl_4F_3O_4$ | Liquid |
| 45 | $C_{24}H_{27}Cl_4NO_3$ | Oil | 46 | $C_{25}H_{29}Cl_4NO_3$ | Oil |
| 47 | $C_{27}H_{31}Cl_4NO_3$ | Oil | 48 | $C_{31}H_{33}Cl_4NO_3$ | Oil |
| 49 | $C_{23}H_{24}Cl_4O_5$ | Oil | 50 | $C_{23}H_{23}Cl_5O_5$ | Oil |
| 51 | $C_{25}H_{27}Cl_5O_4$ | Oil | 52 | $C_{23}H_{23}Cl_4NO_5$ | Oil |
| 53 | $C_{23}H_{23}Cl_4NO_5$ | Solid | 54 | $C_{23}H_{25}Cl_5O_4$ | Oil |

Surface-Treated Diet Test Against Tobacco Budworm

The compounds were evaluated for activity against the tobacco budworm (*Heliothis virescens* [Fabricius]) in a surface-treated diet test.

In this test one mL of molten (65-70° C.) wheat germ-based artificial diet was pipetted into each well of a four by six (24 well) multi-well plate (ID# 430345-15.5 mm dia.×17.6 mm deep; Corning Costar Corp., One Alewife Center, Cambridge, Mass. 02140). The diet was allowed to cool to ambient temperature before treatment with candidate insecticide.

For a determination of insecticidal activity, solutions of the candidate insecticides were prepared for testing using a Packard 204DT Multiprobe® Robotic System (Packard Instrument Company, 800 Research Parkway, Meriden, Conn. 06450), in which the robot first diluted a standard 50 millimolar DMSO solution of candidate insecticide with a 1:1 water/acetone solution (V/V) in a ratio of 1:7 stock solution to water/acetone. The robot subsequently pipetted 40 microliters of the so-prepared solution onto the surface of the diet in each of three wells in the 24 multi-well plate. The process was repeated with solutions of seven other candidate insecticides. Once treated, the contents of the multi-well plate were allowed to dry, leaving 0.25 millimoles of candidate insecticide on the surface of the diet, or a concentration of 0.25 millimolar. Appropriate untreated controls containing only DMSO on the diet surface were also included in this test.

For evaluations of the insecticidal activity of a candidate insecticide at varying rates of application, the test was established as described above using sub-multiples of the standard 50 millimolar DMSO solution of candidate insecticide. For example, the standard 50 millimolar solution was diluted by the robot with DMSO to give 5, 0.5, 0.05, 0.005, 0.0005 millimolar, or more dilute solutions of the candidate insecticide. In these evaluations there were six replicates of each rate of application placed on the surface of the diet in the 24 multi-well plate, for a total of four rates of application of candidate insecticide in each plate.

In each well of the test plate was placed one second instar tobacco budworm larvae, each weighing approximately five milligrams. After the larvae were placed in each well, the plate was sealed with clear polyfilm adhesive tape. The tape over each well was perforated to ensure an adequate air supply. The plates were then held in a growth chamber at 25° C. and 60% relative humidity for five days (light 14 hours/day).

After the five-day exposure period insecticidal activity for each rate of application of candidate insecticide was assessed as percent inhibition of insect weight relative to the weight of insects from untreated controls, and percent mortality when compared to the total number of insects infested.

Insecticidal activity data at selected rates of application from this test are provided in Table 3. The test compounds of formula I are identified by numbers that correspond to those in Table 1.

TABLE 3

Insecticidal Activity of Certain (dihalopropenyl) phenylalkyl substituted dihydrobenzofuran and dihydrobenzopyran derivatives Derivatives When Applied to the Surface of the Diet of Tobacco Budworm (*Heliothis virescens* [Fabricius])

| Cmpd. No. | Percent Mortality | Percent Growth Inhibition | Cmpd. No. | Percent Mortality | Percent Growth Inhibition |
|---|---|---|---|---|---|
| 1 | 100 | 100 | 2 | 100 | 100 |
| 3 | 100 | 100 | 4 | 100 | 100 |
| 5 | 100 | 100 | 6 | 100 | 100 |
| 7 | 100 | 100 | | | |
| 9 | 0 | 78 | 10 | 100 | 100 |
| 11 | 100 | 100 | 12 | 100 | 100 |
| 13 | 100 | 100 | 14 | 100 | 100 |
| 15 | 100 | 100 | 16 | 100 | 100 |
| 17 | 100 | 100 | 18 | 100 | 100 |
| 20 | 100 | 100 | 21 | 100 | 100 |
| 22 | 100 | 100 | 24 | 100 | 100 |
| 25 | 100 | 100 | 27 | 100 | 100 |
| 28 | 100 | 100 | 29 | 100 | 100 |
| 30 | 100 | 100 | 31 | 100 | 100 |
| 32 | 100 | 100 | 33 | 100 | 100 |
| 34 | 100 | 100 | 35 | 100 | 100 |
| 36 | 100 | 100 | 37 | 100 | 100 |
| 38 | 100 | 100 | 39 | 100 | 100 |
| 40 | 100 | 100 | 41 | 100 | 100 |
| 42 | 100 | 100 | 43 | 100 | 100 |
| 44 | 100 | 100 | 45 | 100 | 100 |
| 46 | 100 | 100 | 47 | 100 | 100 |
| 48 | 100 | 100 | 49 | 100 | 100 |
| 50 | 100 | 100 | 51 | 100 | 100 |
| 52 | 100 | 100 | 53 | 100 | 100 |
| 54 | 100 | 100 | | | |

Concentration of the candidate insecticide on the surface of the diet is 0.25 millimolar.

As set forth in the foregoing Table 3, all of the compounds tested provided insecticidal activity, with nearly all providing 100% mortality and 100% growth inhibition of tobacco budworm.

For purposes of comparison, Compound 12 of the present invention was tested in side-by-side tests with certain analogous benzofuranyl derived compounds wherein the test compounds were applied to the foliage of test plants. Compound 12 and the analogous compounds in these tests have the following structure:

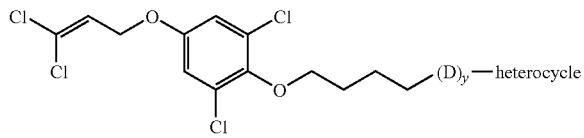

where heterocycle is:

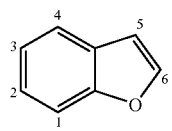

A a benzofuranyl

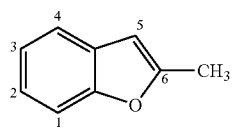

B a methyl-substituted benzofuranyl

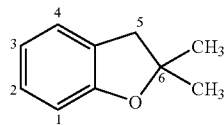

C a dimethyl-substituted 2,3-dihydrobenzofurnayl where y is 1:

| Cmpd. No. | D | Heterocycle | Position of Heterocycle Attachment |
|---|---|---|---|
| 12 | O | C | 1 |
| W | O | A | 1 |
| X | O | B | 1 |
| Y | CH$_2$ | A | 6 |
| Z | O | A | 4 |

Compounds 12, W, X and Y were tested for insecticidal activity in foliar evaluations against tobacco budworm (*Heliothis virescens* [Fabricius]), cabbage looper (*Trichoplusia ni* [Hubner]) and Diamondback Moth (*Plutella xylostella*) using the following methods:

Foliar Treated Test Against Tobacco Budworm and Cabbage Looper

Nine-to-ten day-old chick pea plants (*Cicer arietinum*) were sprayed at 15 psi to runoff on both upper and lower leaf surfaces with solutions of test compound to provide application rates as high as 1000 ppm of test chemical. The solvent used to prepare the solutions of test compound was 10% acetone or methanol (v/v) and 0.1% of the surfactant octylphenoxypolyethoxyethanol in distilled water. Four replicates, each containing one chick pea plant, for each rate of application of test compound were sprayed. The treated plants were transferred to a hood where they were kept until the spray had dried.

The four chick pea plants for each replicate treated with test compound as described above were removed from their pots by cutting the stems just above the soil line. The excised leaves and stems from the four plants in each replicate were placed in individual 237 mL (8-ounce) paper cups, which contained a moistened filter paper. Five second-instar (7 days old) tobacco budworms or cabbage loopers (7 days old) were counted into each cup, taking care not to cause injury. An opaque plastic lid was placed on each cup, which was then held in a growth chamber for a 96 hour exposure period at 25° C., 50% relative humidity and photo-period of 12 hours light and 12 hours dark. At the end of the 96 hour exposure period the cups were opened, and the numbers of dead, moribund, and live insects were counted. Using the insect counts, the efficacy of the test compound was expressed in percent control. Percent control is derived from the total number of dead insects (TD) plus the total number of moribund insects (TM) as compared to the total number of insects (TI) in the test:

$$\% \text{ Control} = \frac{TD + TM}{TI} \times 100$$

The condition of the test plants was also observed for phytotoxicity and for reduction of feeding damage as compared to an untreated control.

Larvae are classified as "moribund" if they fail to rapidly right themselves when turned over, but show movement, or if they are severely reduced in size and do not appear to be feeding.

Results of these tests against tobacco budworm and cabbage looper are set forth below in Table 4.

Foliar Treated Test Against Diamondback Moth

Leaf discs 2.5 cm in diameter were cut from six-week-old cabbage leaves were dipped in solutions of test chemical of various concentrations to provide application rates as high as 1000 ppm of test compound. The solvent used to prepare the solutions of test compound was 10% acetone or methanol (v/v) and 0.1% of the surfactant octylphenoxypolyethoxyethanol in distilled water. Four replicates, each containing one cabbage leaf disc, for each rate of application of test compound were dipped.

The four cabbage leaf discs for each replicate treated were immersed for five seconds in the solution of test compound as described above. Each discs was then placed in individual 50 mm Petrie dishes containing a filter paper 42.5 mm in diameter that had been moistened with 100 μL of water. The uncovered Petrie dishes were then set aside until the leaf discs were dry. After this time, two third-instar diamondback moth larvae (10-14 days old) were carefully placed on each leaf disc. A tight-fitting lid was then placed on each Petrie dish, which was which was then held in a growth chamber for a 96 hour exposure period at 25° C., 50% relative humidity and photo-period of 12 hours light and 12 hours dark. At the end of the 96 hour exposure period the Petrie dishes were uncovered, and the numbers of dead, moribund, and live insects were counted. Using the insect counts, the efficacy of the test compound was expressed in percent control by methods set forth above in tests against the tobacco budworm and cabbage looper.

Results of these tests against diamondback moth are set forth below in Table 4.

TABLE 4

Insecticidal Activity Against Tobacco Budworm, Diamondback Moth and Cabbage Looper on Foliage

| Cmpd. ID | Percent Control at a Rate of Application of 30 ppm | | |
|---|---|---|---|
|  | TBW[1] | DBM[2] | CL[3] |
| Cmpd. 12 | 88 | 91 | 96 |
| Cmpd. W | 62 | 60 | 20 |
| Cmpd. X | 96 | 85 | 50 |
| Cmpd. Y | 5 | Not tested | Not tested |
| Cmpd. Z | 60 | 60 | 20 |

[1]Tobacco Budworm;
[2]Diamondback Moth;
[3]Cabbage Looper;

Analysis of the results of the forgoing tests clearly indicate that, although there is no significant difference between compound 12 and compound X in control of tobacco budworm and diamondback moth, compound 12 is more active against cabbage looper than is compound X. Compound 12 is also more active against all three insect species than are compounds W, Y and Z. Thus, when compared to certain analogous benzofuranyl derived compounds, compound 12 of the present invention provides at least equal or unexpectedly better control of a broader spectrum of insect species than does the aforementioned benzofuran derivatives.

Whole Plant Foliar Treated Test Against Cabbage Looper

For each rate of application of test compound, a 15 mL aliquot of test solution was prepared. Sufficient test compound was dissolved in 1.5 mL of acetone to provide an application rate as high as 1000 grams/Ha. Each solution was then added to 13.5 mL of water containing 300 ppm of a surfactant. There were four replicates for each rate of application of test compound, and all tests included a known chemical standard as well as a standard of water and surfactant and untreated checks.

A maximum of 14 appropriately sized cabbage plants for each rate of application and replicate were arranged in a 28 pot plastic flat and sprayed with the 15 mL sample of test compound using an traveling boom sprayer equipped with a cone spray tip at a rate of 30 gallons/acre under a pressure of 40-44 psi. The untreated checks were sprayed first, followed by the test compounds and standards, all in order of lowest to highest rates of application. Once the spraying was complete, the test plants were allowed to air-dry on the conveyor on which they were sprayed.

For each rate of application and replication, sufficient Petrie dishes, 50×9 mm in size, were lined with filter paper disks and each were moistened with 0.5 mL of distilled water. From each replicate cabbage plant at least three 2.5 cm disks were cut Each leaf disk was then placed in an individual Petrie dishes with the adaxial side of the leaf facing up. Following placement of the leaf disks, two neonate cabbage looper larvae were placed on each disk. Upon completion of infestation each Petrie dish was covered and held in a growth chamber for a 96 hour exposure period at 25° C., 40%-60% relative humidity and photo-period of 12 hours light and 12 hours dark. At the end of the 96 hour exposure period the Petrie dishes were opened, and the numbers of dead, moribund, and live insects were counted. Using the insect counts, the efficacy of the test compound was expressed in percent control. Percent control is derived from the total number of dead insects (TD) plus the total number of moribund insects (TM) as compared to the total number of insects (TI) in the test:

$$\% \text{ Control} = \frac{TD + TM}{TI} \times 100$$

The condition of the test plants was also observed for phytotoxicity and for reduction of feeding damage as compared to an untreated control. Larvae are classified as "moribund" if they fail to rapidly right themselves when turned over, but show movement, or if they are severely reduced in size and do not appear to be feeding. Results of these tests are set forth in Table 5

TABLE 5

Insecticidal Activity Against Cabbage Looper on Foliage

| Cmpd. ID | Percent Control at Indicted Rate of Application | | |
|---|---|---|---|
|  | 100 g | 50 g | 25 g |
| Cmpd. 12 | 100 | 100 | 88 |
| Cmpd. X | 13 | 8 | 8 |

These results clearly indicate that compound 12 is more active against cabbage looper than is compound X.

Photostability

Again, for purposes of comparison, compound 12 of the present invention was tested in side-by-side tests with analogous benzofuranyl derived compounds designated as compounds W, X, Y and Z as set forth above to determine their photochemical stability, i.e., their rate of photolysis. These tests were conducted in the following manner:

For each compound tested, three glass microscope coverslips (12 mm in diameter) for each illumination period (1, 3, 6, 12, and 24 hours) were spotted with 10 microliters of a one mg/mL acetonitrile or methanol solution of test compound. Three coverslips were also spotted with test compound and were not illuminated. The material on these non-illuminated coverslips was analyzed at the end of the experiment as described below to determine the test compound stability on glass. The solvents in each 10 microliter solution on each coverslip were allowed to evaporate leaving a thin film of test compound on each coverslip. Three of the coverslips representing the zero hour illumination period were then placed in a 20 mL scintillation vial. In the vial was placed one mL of acetonitrile, which extracted the test chemical from the coverslip. The solution was then transferred to a two-dram vial for analysis by HPLC. The average HPLC peak area generated by this sample defined the initial level of test compound. The remaining coverslips were then placed in the water-cooled chamber of the exposure platform of a Suntest CPS illuminator (Heraeus Instruments GmbH; Bereich Original Hanau, Hersaeusstrasse R-14, Postfach 1563, D-6450 Hanau 1). The exposure platform was covered with a quartz plate and maintained at about 25° C. for the duration of the test. The Suntest CPS illuminator employs a filtered xenon lamp, which provides illumination of a similar spectrum and intensity as sunlight. Three coverslips for each test compound were removed from the illuminator at 1, 3, 6, 12, and 24 hours of continuous illumination. Approximately eight hours of illumination is equivalent to one summer day at 40° N latitude. The three coverslips from each of the illumination periods were treated as described above and analyzed by HPLC. The average HPLC peak area from each of these illumination periods represents a diminished amount of test compound when compared to the initial level of test compound as determined from the zero hour illumination sample. The percents of test compound remaining from each of these illumination periods were used to generate a degradation curve from which a half-life in hours was determined for each test compound. The relative half-lives for each compound compared to that of compound 12 were then calculated as a percent of compound 12 half-life. Results of these tests are set forth in Table 6 below:

TABLE 6

| | Photostability in Half-life Hours | |
|---|---|---|
| Cmpd. No | Photolysis Half-life (Hours) | Percent of Compound 12 Half-life |
| 12 | 19 | 100% |
| W | 11 | 58% |
| X | 6 | 32% |
| Y | 4 | 21% |
| Z | 4 | 21% |

Analyses of the results of the forgoing tests clearly indicate that compound 12 is more photostable than any of the benzofuranyl derivatives. Compound W, the most photostable benzofuranyl derivative tested, is only a little more than half (58%) as photostable as is compound 12.

While this invention has been described with an emphasis upon preferred embodiments, it will be understood by those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A compound of formula I:

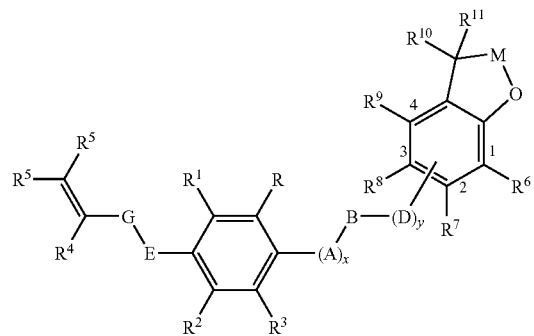

R and $R^3$ are independently selected from the group consisting of hydrogen, halogen, hydroxy, $(C_1-C_3)$alkyl, $(C_3-C_6)$cycloalkyl, $(C_2-C_5)$alkenyl, $(C_2-C_5)$alkynyl, halo$(C_1-C_3)$alkyl, $(C_1-C_3)$alkoxy, halo$(C_1-C_3)$alkoxy, $(C_1-C_3)$alkylthio, halo$(C_1-C_3)$alkylthio, $(C_1-C_3)$alkylsulfonyl, halo$(C_1-C_3)$alkylsulfonyl, cyano, nitro; optionally substituted amino wherein the optional substituent is selected from $(C_1-C_4)$alkyl, $(C_1-C_3)$alkylcarbonyl and $(C_1-C_3)$alkoxycarbonyl; optionally substituted imidazolyl, optionally substituted imidazolinyl, optionally substituted oxazolinyl, optionally substituted oxazolyl, optionally substituted oxadiazolyl, optionally substituted thazolyl, optionally substituted pyrazolyl, optionally substituted triazolyl, optionally substituted furanyl, optionally substituted tetrahydrofuranyl, optionally substituted dioxolanyl, optionally substituted dioxanyl, —C(=J)-K, and —C($R^{12}$)-Q-$R^{13}$, wherein the optional substituent is selected from $(C_1-C_4)$alkyl, halo(C1-C4)alkyl, $(C_1-C_4)$alkoxy, $(C_1-C_4)$alkoxy$(C_1-C_4)$alkyl, (C3-C6)cycloalkyl, $(C_2-C_5)$alkenyl, $(C_2-C_5)$alkynyl, cyano, nitro and aryl;

where

J is selected from the group consisting of O, S, $NR^{14}$, and $NOR^{14}$, where $R^{14}$ is hydrogen, $(C_1-C_4)$alkyl, halo$(C_1-C_4)$alkyl, aryl and aryl$(C_1-C_4)$alkyl;

K is selected from the group consisting of hydrogen, $(C_1-C_3)$alkyl, halo$(C_1-C_3)$alkyl, $(C_1-C_3)$alkoxy, $(C_1-C_3)$alkylamino and di$(C_1-C_3)$alkylamino;

Q is selected from the group consisting of O, S, and $NR^{14}$, where $R^{14}$ is previously described;

$R^{12}$ and $R^{13}$ are independently selected from the group consisting of hydrogen, $(C_1-C_4)$alkyl and halo$(C_1-C_4)$alkyl, and $R^{12}$ and $R^{13}$ may be taken together with -T(CH$R^{14}$)m, where m is an integer of 2 to 4; T is selected from O, S, and $NR^{14}$, where $R^{14}$ is as previously described;

$R^1$ and $R^2$ are independently selected from the group consisting of hydrogen, halogen and $(C_1-C_3)$alkyl $R^4$ is hydrogen;

$R^5$'s are independently selected from halogen;

E is selected from the group consisting of $CH_2$, O, S and $NR^{15}$ where $R^{15}$ is selected from the group consisting of hydrogen, $(C_1-C_3)$alkyl, $(C_1-C_3)$alkoxy$(C_1-C_3)$alkyl, aryl$(C_1-C_3)$alkyl, $(C_2-C_4)$alkenyl$(C_1-C_3)$alkyl, halo $(C_2-C_4)$alkenyl$(C_1-C_3)$alkyl, di$(C_1-C_3)$alkylphosphonate, formyl, $(C_1-C_3)$alkylcarbonyl, halo$(C_1-C_3)$alkylcarbonyl, $(C_1-C_3)$alkoxy$(C_1-C_3)$alkylcarbonyl, arylcarbonyl and $(C_1-C_3)$alkylsulfonyl;

G is selected from the group consisting of O, S, $CH_2O^*$ and $(CH_2)_n$ where the asterisk denotes attachment to E, and n is an integer selected from 1, or 2, provided that E and G are not simultaneously O or S, x is an integer selected from 0 or 1;

and when x is 1,

A is selected from O, $S(O)_p$ and —$NR^{15}$, where p is an integer selected from 0, 1 and 2, and $R^{15}$ is as previously described;

B is a bridging group,

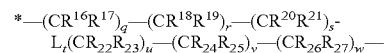

where the asterisk denotes attachment at A; q, r, s, u, v and w are integers independently selected from 0, 1 and 2;

and when q, r, s, u, v or w are 1 or 2, $R^{16}$ through $R^{27}$, inclusively, are hydrogen;

t is 0;

y is an in integer selected from 0 or 1;

and when y is 1,

D is selected from O; $S(O)_p$; and $NR^{15}$, where p and $R^{15}$ are as previously described, and wherein D is attached to the benzo-fused ring moiety set forth in formula I at positions 1:

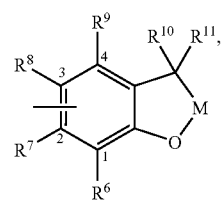

$R^7$, $R^8$ and $R^9$ are independently selected from the group consisting of hydrogen, halogen, $(C_1-C_4)$alkyl, $(C_3-C_6)$cycloalkyl, $(C_2-C_5)$alkenyl, $(C_2-C_5)$alkynyl, halo$(C_1-C_4)$alkyl, $(C_1-C_4)$alkoxy, halo$(C_1-C_4)$alkoxy, $(C_1-C_4)$alkylthio, halo$(C_1-C_4)$alkylthio, $(C_1-C_4)$alkylsulfonyl, halo$(C_1-C_4)$alkylsulfonyl, cyano, nitro, aryl, alkylcarbonylamino, arylcarbonylamino, and $(C_1-C_4)$alkoxycarbonylamino;

$R^{10}$ and $R^{11}$ are independently selected from the group consisting of hydrogen, halogen, hydroxyl, alkyl, alkoxy, or $R^{10}$ and $R^{11}$ taken together are O forming a carbonyl group; $OCH_2CH_2O$ or $SCH_2CH_2S$ forming a ketal or a thioketal group; or $NOR^{15}$ forming an oxime, where $R^{15}$ is as previously described;

M is *$C(R^{32}R^{33})$ where the asterisk indicates attachment to O and wherein $R^{32}$ and $R^{33}$ independently are selected from the group consisting of hydrogen, halogen, $(C_1-C_4)$alkyl, $(C_1-C_4)$alkoxy$(C_1-C_4)$alkyl, and halo$(C_1-C_4)$alkyl, or agriculturally acceptable salts thereof.

2. A compound of claim 1, wherein R and $R^3$ are independently selected from the group consisting of halogen and $(C_1-C_3)$alkyl;

$R^1$, $R^2$, and $R^4$ are hydrogen;

$R^5$'s are independently selected from chlorine, bromine, and fluorine;

E is O;

G is $(CH_2)_n$, where n is 1;

x is 1, and A is O;

y is 1, and D is selected from the group consisting of O; S(O)p; and $NR^{15}$, where p is 0, and $R^{15}$ is selected from the group consisting of hydrogen, $(C_1C_3)$alkyl, aryl$(C_1-C_3)$alkyl, $(C_2-C_4)$alkenyl$(C_1-C_3)$alkyl, and halo$(C_2-C_4)$alkenyl$(C_1-C_3)$alkyl, wherein D is attached to the benzo-fused moiety set forth in formula I at the position designated 1;

$R^6$, $R^7$, $R^8$ and $R^9$ are independently selected from the group consisting of hydrogen, halogen, halo$(C_1-C_4)$alkyl and nitro;

$R^{10}$ and $R^{11}$ are hydrogen, or $R^{10}$ and $R^{11}$ are taken together with O to form a carbonyl group;

and $R^{32}R^{33}$ are independently $(C_1-C_4)$alkyl.

3. A compound of claim 1, wherein the compound is selected from the group consisting of

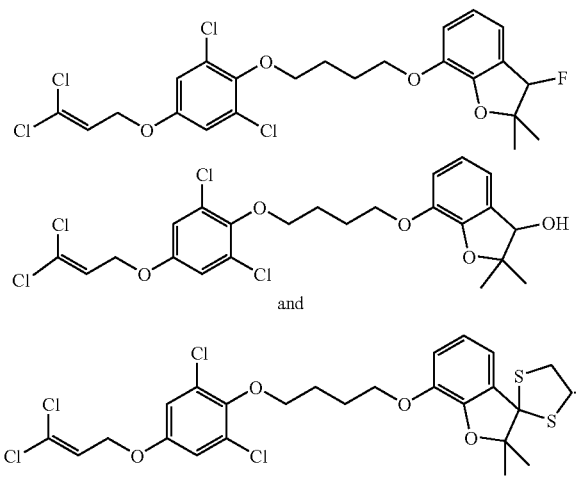

* * * * *